United States Patent
Ogata et al.

[11] Patent Number: 5,017,708
[45] Date of Patent: May 21, 1991

[54] AZABICYCLOALKANES

[75] Inventors: Masaru Ogata, Hyogo; Hiroshi Matsumoto, Osaka; Sumio Shimizu, Hyogo; Shiro Kida, Osaka, all of Japan

[73] Assignee: Shionogi & Co., Ltd., Osaka, Japan

[21] Appl. No.: 404,449

[22] Filed: Sep. 8, 1989

[30] Foreign Application Priority Data

Sep. 12, 1988 [JP] Japan .................... 63-227697

[51] Int. Cl.$^5$ ............ C07D 209/52; C07D 209/46; C07D 209/48; C07D 209/44

[52] U.S. Cl. .................... 548/515; 540/203; 540/593; 540/594; 546/153; 546/155; 546/158; 546/164; 546/141; 546/142; 546/143; 546/146; 546/150; 546/183; 548/452; 548/512; 548/513; 548/950; 548/952; 548/953

[58] Field of Search ............... 548/452, 512, 513, 515

[56] References Cited

U.S. PATENT DOCUMENTS

| | | | |
|---|---|---|---|
| 2,858,314 | 10/1958 | Georgian | 548/439 |
| 3,252,972 | 5/1966 | Mull | 548/515 |
| 3,522,240 | 7/1970 | Mull | 260/239 |
| 3,972,994 | 8/1976 | Beregi et al. | 424/274 |
| 3,983,249 | 9/1976 | Ehrreich | 514/412 |
| 4,591,593 | 5/1986 | Yokoyama | 548/515 |

FOREIGN PATENT DOCUMENTS 0090362 10/1983 European Pat. Off. .
2415064 10/1974 Fed. Rep. of Germany .

OTHER PUBLICATIONS

Oida, Chem. Abs. 103, 16329v (1985).
Achini, Chem. Abs. 81, 13412h (1974).
Chiusoli, Chem. Abs. 105, 172283 (1986).
Schenker, Chem. Abs. 71, 38451b (1968).
Armarego, Chem. Abs. 75, 140135w (1971).
Chiba, Chem. Abs. 111, 153779w (1979).
Bellasio, Chem. Abs. 80, 146097k
Zinner, Chem. Abs. 70, 37641f.
Murayama et al., Chemical Abstracts, vol. 62, No. 13, Jun. 21, 1965, column 16173F-16174G.
Booth et al., Jounral Chem. Soc., 1959, pp. 1050-1054.
Beugelmans et al., Chemical Abstracts, vol. 103, No. 3, Jul. 22, 1985, p. 559, column 2, Abstract No. 22404g.

Primary Examiner—Mark L. Berch
Attorney, Agent, or Firm—Wenderoth, Lind & Ponack

[57] ABSTRACT

A compound of the formula:

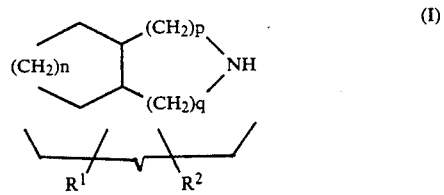

wherein $R^1$ and $R^2$ each is hydrogen, hydroxy, oxo, halogen, azido, amino, $C_1$-$C_3$ alkylamino, or aminomethyl, in which said amino, $C_1$-$C_3$ alkylamino and aminomethyl each is optionally substituted by one or two members selected from the group consisting of $C_1$-$C_3$ alkyl and amino-protecting group; n is an integer of 1 to 3; p and q each is an integer of 0 to 3 with proviso that p+q=1 to 4 or acid-addition salts thereof, being useful materials for preparing side chains of antibacterial quinolonecarboxylic acids, cephalosporines, or other antibiotics.

12 Claims, No Drawings

AZABICYCLOALKANES

BACKGROUND OF THE INVENTION

1. Field of the Invention

This invention relates to azabicycloalkanes.

2. Prior Art

Some azabicycloalkanes have heretofore been known [O. Tsuge et al., Bull. Chem. Soc. Jpn., 60, 4079–4089 (1987)]. However, there is no disclosure on the subject matter of the present invention in said literature.

SUMMARY OF THE INVENTION

This invention relates to azabicycloalkanes which are useful for preparing side chains of antibacterial quinolonecarboxylic acids, cephalosporins, or other antibiotics. For example, excellent antibacterial agents can be prepared by reacting the objective compound (I) with 7-halo-quinolonecarboxylic acid (U.S. patent application Ser. No. 07/353,321).

DETAILED DESCRIPTION

This invention relates to compounds of the formula:

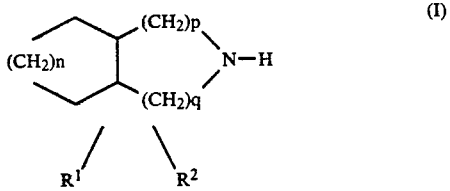

wherein $R^1$ and $R^2$ each is hydrogen, hydroxy, oxo, halogen, azido, amino, $C_1$-$C_3$ alkylamino, or aminomethyl, in which said amino, $C_1$-$C_3$ alkylamino and aminomethyl each is optionally substituted by one or two substituent selected from $C_1$-$C_3$ alkyl and amino-protecting group; n is an integer of 1 to 3; p and q each is an integer of 0 to 3 with proviso that p+q=1 to 4 or acid-addition salts thereof.

In the specification, $C_1$-$C_3$ alkylamino includes methylamino, ethylamino, propylamino, and isopropylamino.

$C_1$-$C_3$ alkyl includes methyl, ethyl, n-propyl, and isopropyl.

Amino-protecting group includes lower alkanoyl such as formyl, acetyl, propionyl, butyryl, or isobutyryl, benzoyl, lower alkoxycarbonyl such as methoxycarbonyl, ethoxycarbonyl, propoxycarbonyl, or t-butoxycarbonyl, benzyloxycarbonyl, trityl, and the like.

Halogen includes fluorine, chlorine, bromine, and iodine.

Amino, $C_1$-$C_3$ alkylamino and aminomethyl may be substituted by one or two substituents selected from $C_1$-$C_3$ alkyl and amino-protecting group.

The compound (I) of this invention can be prepared by the following reaction scheme:

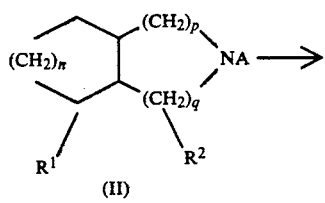

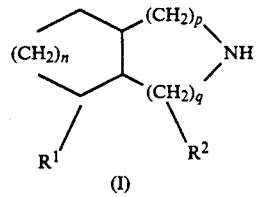

wherein $R^1$, $R^2$, n, p, and q have the same significance as defined above, and A is amino-protecting group.

The compound (I) of the present invention can be prepared by subjecting the compound (II) to deprotection for removal of the amino-protecting group. Thus, the deprotection may be carried out by chemical means generally adopted for removal of the amino-protecting group, depending upon the sort of amino-protecting group.

In case the protecting group is lower alkanoyl, lower alkoxycarbonyl, or trityl, the deprotection can be performed in a conventional manner by treating the compound (II) with a base such as sodium hydroxide, potassium hydroxide, or calcium hydroxide or an acid such as hydrochloric acid, sulfuric acid, acetic acid, or trifluoroacetic acid in a solvent such as water, aqueous alcohol (e.g. aqueous methanol, aqueous ethanol) or aqueous acetic acid at a temperature from around room temperature to the boiling point of the solvent used.

In case the protecting group is benzyloxycarbonyl, the deprotection can be performed in a conventional manner by hydrogenating the compound (II) over a catalyst such as palladium-carbon, platinum, nickel, or cobalt in a solvent such as methanol or ethanol at a temperature from room temperature to the boiling point of the solvent used, under 1 to 10 atmosperic pressure. When another substituent sensitive to the deprotection exists in the compound (II), such a substituent may be possibly influenced by said deprotection. The compound (II) having azido other than benzyloxycarbonyl may be reduced at a time to give the compound qI) having amino together with removal of the benzyloxy group.

Of the compounds of the present invention, the compound (I a), (I b), and ( I c) are preferred as shown below.

(1) Compound (I a):

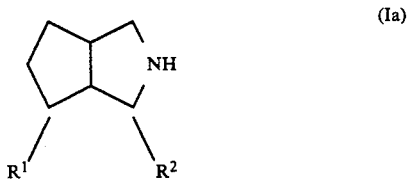

wherein $R^1$ and $R^2$ each is hydrogen, hydroxy, oxo, amino or aminomethyl in which said amino and aminoethyl is optionally substituted by one or two members selected from the group consisting of lower alkyl, lower alkanoyl and lower alkoxycarbonyl.

(2) Compound (I b ):

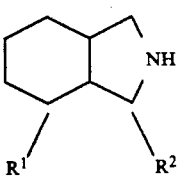

(Ib)

wherein R¹ and R² each is hydrogen, hydroxy, or amino optionally substituted by one or two members selected from the group consisting of lower alkyl, lower alkanoyl and lower alkoxycarbonyl.

(3) Compound (I C):

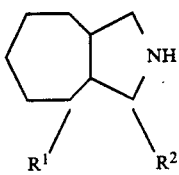

(Ic)

wherein R¹ and R² each is hydrogen, hydroxy, or amino optionally substituted by one or two members selected from the group consisting of lower alkyl, lower alkanoyl and lower alkoxycarbonyl.

More preferably compounds of this invention will be shown below:
6-hydroxy-3-azabicyclo[3,3,0]octane;
6oxo-3-azabicyclo[3,2,0]octane;
7-amino-3-azabicyclo[3,3,0]octane;
6-acetylamino-3-azabicyclo[3,3,0]octane;
6-(N-methylacetylamino)-3azabicyclo[3,3,0]octane;
1-ethoxycarbonylamino-3-azabicyclo[3,3,0]octane;
6-amino-5-hydroxy-3azabicyclo[3,3,0]octane;
6-aminomethyl-3-azabicyclo[3,3,0]octane;
1-acetylaminomethyl-3-azabicyclo[3,3,0]octane;
1-(N-formyl-N-methyl-aminomethyl)-3-azabicyclo[3,3,-0]octane;
1-(N-formyl-N-ethyl-aminomethyl)-3-azabicyclo[3,3,-0]octane;
2-amino-8-azabicyclo4,3,0]nonane;
2-formylamino-8-azabicyclo[4,3,0]nonane;
2-(N-methylformylamino)-8azabicyclo[4,3,0]octane;
2-(N-methyl-t-butoxycarbonlamino)-8azabicyclo[4,3,0-]nonane;
2-amino-9-azabicyclo[5,3,0]decane;
2-formylamino-9-azabicyclo[5,3,0]decane;
2(N-methyl-t-butoxycarbonylamino)-9-azabicyclo[5,3,0 decane;
2-t-butoxycarbonylamino)-9-azabicyclo[5,3,0]decane; and
4-aminooctahydroindole.

The compound (I) may be, if necessary, converted into its acid addition salts. Examples of such an acid which can form a salt are an inorganic acid (e.g. hydrochloric acid, hydrobromic acid, sulfuric acid, etc.) and an organic acid (e.g. trifluoroacetic acid, acetic acid, oxalic acid, tartaric acid, phtalic acid, succini acid, etc.).

Illustrative preparation of the starting compounds (II) is to be referred to Reference Examples as shown below.

Presently-preferred and practical embodiments of the present invention are illustratively shown in the following examples.

The abbreviations used in the examples and reference examples have the following means.

Me: Methyl
Et: Ethyl
Ac: Acetyl
Ph: Phenyl
Ps:-Toluenesulfonyl
Tr: Triphenylmethyl
Ms: Mesyl
BOC: t-Butyloxycarbonyl
DMF: Dimethylformamide
THF: Tetrahydrofuran
DMSO: Dimethyl sulfoxide
HMPA: Hexamethylphosphoric triamide
Z: Benzyloxycarbonyl

EXAMPLE 1

(1R*,5R*,6S*) -6Hydroxy-3-azabicyclo[3,3,0]octane (I a-1)

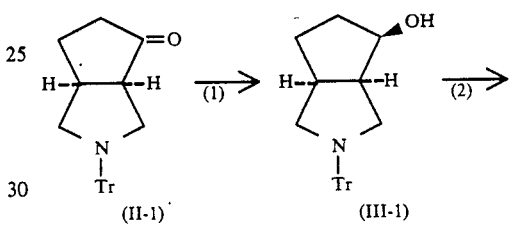

(1) To a solution of 1.0 g of the compound (II -1) in 20 of methanol-methylene chloride (1:1 v/v) is added 106 mg of NaBH₄, and the reaction mixture is stirred at room temperature for 10 minutes. The solution is acidified with acetic acid under ice-cooling and basified with aqueous NaHCO₃. The solution is extracted with methylene chloride, and the organic layer is washed with water, dried over Na₂SO₄ and concentrated. The resulting residue is subjected to silica gel column chromatography, eluting with 3% methanol-methylene chloride, and the eluate is concentrated to give 900mg (Yield : 90%) of the compound (III -1).

mp. 150°–152° C.

IR (film): 3400 cm⁻¹.

¹HNMR (CDCl₃)δ: 1.40–3.20 (m. 10H); 3.55 (bs 1H); 4.21 (bs. 1H); 7.05–7.50 (m 15H)

(2) A solution of 1 g of the compound (III -1) in 5.0 ml of aqueous CF₃COOH is heated on water bath. After cooling, the solution is extracted with ethyl acetate, and the aqueous layer is mixed with c-HCl and concentrated under reduced pressure. The resulting residue is washed with either and collected by filtration to give 320 mg (Yield : 70%) of the compound (I a-1) as hygroscopic crystals. mp. 119°–120° C.

¹HNMR(d₆DMSO)δ: 1.5–1.9 (M, 4H); 2.6–3.5 (m, 2H); 4.30 (brs, 1H); 8.90 (brs, 1H); 9.55 (brs, 1H).

EXAMPLE 2

(1R*, 5S*)-6-Oxo-3-azabicyclo[3,3,0]octane (I a-2)

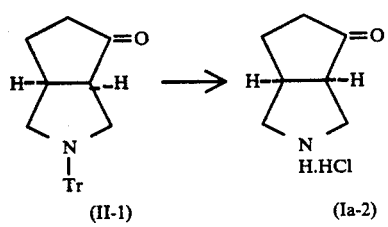

A solution of 750 mg of the compound (II -1) in 6 ml of aqueous CF₃COOH is heated on water bath. After cooling, the mixture is extracted with c-HCl and ethyl acetate in order. The resulting aqueous layer is concentrated under reduced pressure to give 349 mg of the compound (I a-2) as an oil.

IR (film): 2900, 2700, 1730 cm$^{-1}$.
$^1$HNMR (CD$_{3}$ $_{ql}$ $_{OD}$)δ: 1.40–3.60 (m, 10H).

EXAMPLE 3

(1R*, 5S*, 6S*)-6-Acetylamino-3iazabicyclo[3,3,0]octane (I a-3)

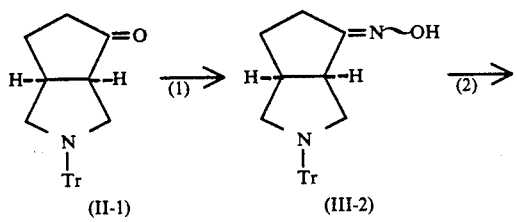

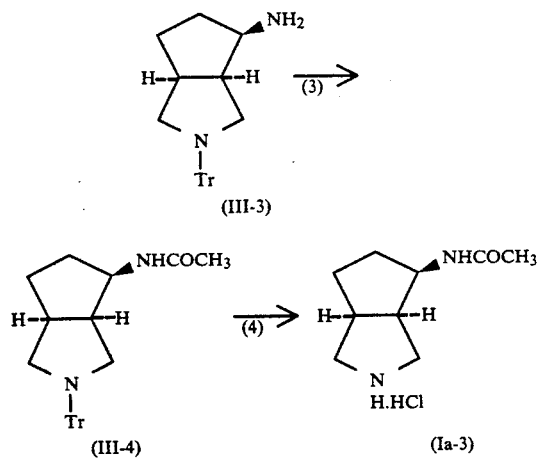

(1) To a solution of 2 g of the compound (II -1) in 20 ml of methanol-methyelene chloride (1:1 v/v) are added 570 mg of NH₂OH—HCl and 670 mg of sodium acetate, and the mixture is refluxed on water bath. After cooling, the mixture is mixed with aqueous NaHCO₃ and extracted with methylene chloride. The organic layer is washed with water, dried over Na₂SO₄ and concentrated to give 2.0 g of the compound (III -2) as an oil.

$^1$HNMR (CDCl₃)δ: 1.70–3.40 (m, 10H); 7.05–7.55 (m, 15H); 8.20 (br, 1H).

(2) To a solution of 1.4 g of the compound (III -2) in dry THF is added 280 mg of LiAlH₄, and the mixture is refluxed for 1.5 hours. After cooling, the solution is mixed with water and filtered. The filtrate is concentrated, and the residue is dissolved in methylene chloride and dried over Na₂SO₄. The solvent is evaporated to give 910 mg of the objective compound (III -3) as an oil.

(3) To a solution of 910 mg of the compound (III -3) in 18 ml of dry methylene chloride are added 780 mg of Et₃N and sucessively under ice-cooling a solution of 400 mg of acetyl chloride in 2 ml of dry methylene chloride. The mixture is stirred at roolm temperature for 15 minutes, mixed with aqueous NaHCOl₃ and extracted with methylene chloride. The organic layer is washed with water, dried over Na₂SO₄, and concentrated. The residue is subjected to silica gel column chromatography, eluting with 2% methanol-methylene chloride to give the objective substance. The resulting substance is recrystallized from ethyo acetate-isopropyl ether to give 780 mg of the compound (III -4) mp. 230°–240° C.

IR (Nujol): 3240, 1630 cm$^{-1}$. $^1$HNMR (CDCl₃)δ: 1.10–2.80 (m, 10H); 1.95 (s, 3H); 4.20 (m, 1H); 5.80 (m, 1H); 7.10–7.70 (m, 15H).

(4) A solution of 740 mg of the compound (III -4) in 10 ml of aqueous CF₃COOH is heated on water bath. After cooling, the solution is extracted with c-HCl and ethyl acetate. The aqueous layer is concentrated under reduced pressure to give 400 mg of the objective compound (I a-3) as an oil.

$^{14}$HNMR (d₆-DMSO)δ: 1.00–3.50 (m, 10H); 1.85 (s, 3H); 4.10 (brs, 1H); 8.25 (brs, 1H); 9.60 (brs, 2H).

EXAMPLE 4

(1R*, 5S*, 6S*)-6-(N-Methlaceylamino)-3-azabicyclo[3,3,0]octane (Ia-4)

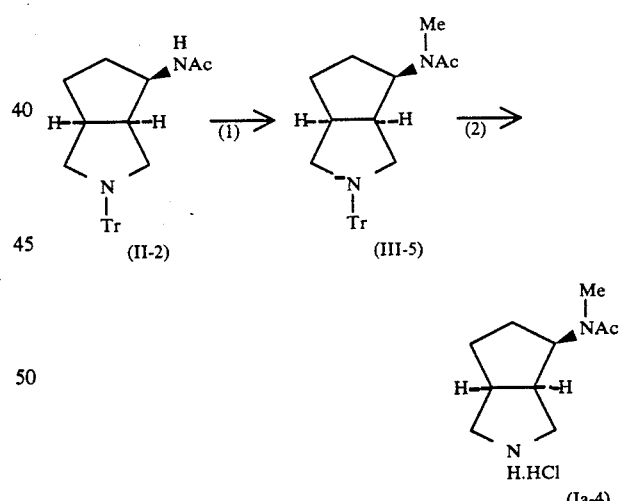

(1) To a solution of 800 mg of the compound (II -2) in 8 ml of dry DMF is added 120 mg of NaH (60% dispersion in mineral oil) with stirring, and the mixture is allowed to stand for 10 minutes. The reaction mixture is mixed with 430 mg of MeI, stirred at 50° C. for 15 minutes and concentrated under reduced pressure. The resulting resudue is mixed with water and extracted with methylene chloride. The organic layer is washed with water, dried over Na₂SO₄ and concentrated. The residue is chromatographed on a colunn of silica gel, eluting with 3% methanol-methylene chloride to give 800 mg of the compound (III -5) as an oil).

IR (film) : 1675, 1640 cm$^{-1}$. $^1$HNMR (CDCl$_3$)δ: 1.30–3.20 (m, 11H); 1.98 (s, 3H); 2.78 (s, 3H); 2.78 (s, 3H); 6.70–7.90 (m, 15H).

(2) A solution of 800 mg of the compound (III -5) in 10 ml of aqueous CF$_3$COOH is heated on water bath. After cooling, the mixture is mixed with c-HCl and washed with ether. The aqueous layer is concentrated under reduce pessure to give 400 mg of the objective compound (I a-4) as an oil. $^1$HNMR (CD$_3$OD)δ: 1.70–3.90 (m, 10H); 2.42 (s, 3H); 3.28 (s, 3H); 4.40 (brs, 1H).

EXAMPLE 5

(1R*, 5S*, 6S*)-6-Amino-5-hydroxy-3-azabicyclo[3,3,0]octane (Ia-5)

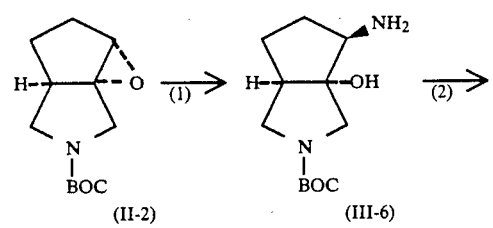

(1) A solution of 415 mg of the compound (II -2), 8 ml of 28% aqueous ammonia and 6 ml of methanol is allowed to stand at room temperature for 17 hours. The mixture is concentrated under reduced pressure to give 463 mg of crude amino alcohol (II-6), $^1$HNMR (cdcL$_3$)δ: 1.22–1.65 (m, 1H); 1.45 (s, 9H); 1.65–2.20 (m, 6H); 2.29–2.45 (m, 1H); 3.16–3.40 (m, 3H); 3.51–3.77 (m, 2H)

(2) A mixture of 400 mg of the compound (III-6) in 15 ml of 2.5M hydrochloric acid-ethyl acetate is stirred at room temperature for 30 minutes, and concentrated under reduced pressure to give the objective compound (I a-5) quantitatively.

$^1$HNMR (CD$_{3ql\ OD}$)δ: 1.45–2.40 (m, 4H); 2.25–2.98 (m, 1H); 3.01–3.97 (m, 5H).

EXAMPLE 6

(1R*, 5R*, 6S*)-6-Amino-5-hydroxy-3-azabicyclo[3,3,0]octane (Ia-6)

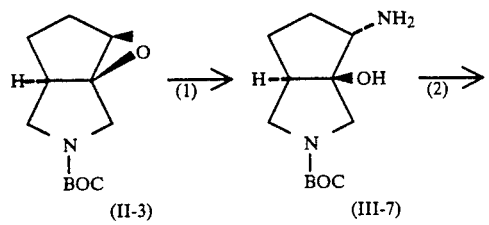

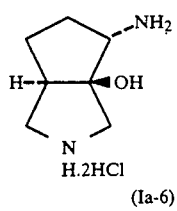

(1) A solution of 430 mg of the compound (II -3), 8 ml of 28% aqueous ammonia and 6 ml of methanol is allowed to stand at room temperature for 6 days and concentrated under reduced pressure to give 468 mg of crude amino alcohol (III -7). $^1$HNMR (CDCl$_3$)δ: 1.10–2.28 (m, 6H); 1.46 (s, 9H); 2.37–2.79 (m, 2H); 3.01–4.08 (m, 5H).

(2) A solution of 468 mg of the compound (III -7) in 20 ml of 2.5M. HCl-ethyl acetate is stirred ar room temperature for 30 minutes, and concentrated under reduced pressure to give the objective compound (Ia-6) quantitatively.

$^1$HNMR (CD$_3$OD)δ: 1.40–2.36 (m, 4H); 2.70–4.38 (m, 6H).

EXAMPLE 7

6-Aminomethyl-3-azabicyclo[3,3,0]octane (Ia-7)

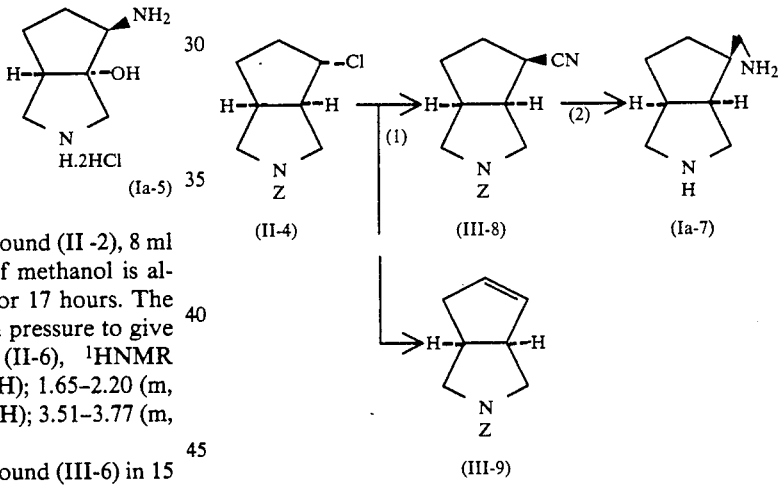

(1) A mixture of 3.4 g of the compound (II -4), 6.0 g of sodium cyanide, 25 ml of DMSO, and 5 ml of HMPA is stirred at 140° C. for 7 hours under heating. The reaction mixture is poured into ice water, and the mixture is extracted with ether. The ether layer is washed with water, drived over MgSO$_4$, and concentrated under reduced pressure. The residue is subjected to silica gel column chromatography, eluting with toluene-ethyl acetate (4:1 v/v) to give 705 mg (Yield : 21%) of the cyano compound (III-8), and eluting with toluene-ethyl acetate (10:1 v/v) to give 1.67 g (Yield : 56%) of the syclic olefine (III- 9). compound (III-8)

$^1$HNMR (CDCl$_3$) δ: 1.42–2.18 (m, 3H); 2.72–3.06 (m, 3H); 3.20–3.48 (m, 1H); 3.48–3.84 (m, 3H); 5.14 (s, 2H); 7.27–7.46 (m, 5H).

compound (III-9).

$^1$HNMR (CDCl$_3$) δ: 2.11–2.32 (m, 1H); 2.48–2.65 (m, 1H); 2.78–3.15 (m, 2H); 3.27–3.81 (m, 4H); 5.47–5.76 (m, 2H); 7.38–7.52 (m, 5H).

(2) A solution of 950 mg of cyano compound (III-8) in 50 ml of ethanol is hydrogenated over 600 mg of 10%

Pd-C at room temperature under atmospheric pressure. After removal of the catalyst, the filtrate is concentrated under reduced pressure. The residue obtained is dissolved in 10 ml of ether, and this solution is poured into a suspension of 266 mg of LiAlH₄ in 10 ml of ether with stirring at below 10° C. This suspension is stirred at room temperature for 3 hours, refluxed under heating for 1 hour and mixed with 10 ml of THF containing 450 mg of water. The mixture is filtered to remove the precipitating inorganic solid, and the filtrate is concentrated under reduced pressure to give 351 mg (Yield: 71%) of the objective compound (Ia-7).

¹HNMR (CDCl₃) δ: 1.04–2.07 (m, 9H); 2.31–2.44 (m, 1H); 2.49–2.70 (m, 3H); 2.75 (d, 2H, J=7.6 Hz); 2.85–3.07 (m, 1H); 3.18–3.32 (m, 1H).

EXAMPLE 8

(1R*,5S*)-7-Amino-3-azabicyclo[3,3,0]octane (Ia-8)

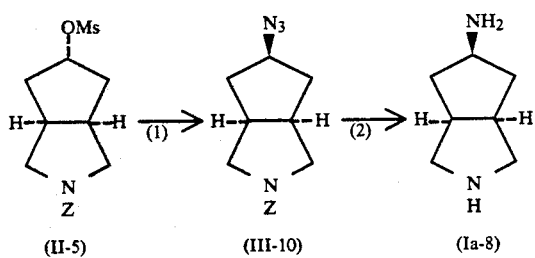

(1) A mixture of 409 mg of the compound (II-5), 235 mg of sodium azide, 1 ml of water, and 5 ml of DMF is stirred at 120° C. for 1.5 hr. The reaction mixture is poured into iced water, and the mixture is extracted with ether. The ether layer is washed with water, dried over MgSO₄ and concentrated under reduced pressure to give 326 mg (Yield: 94%) of the objective azide (III-10).

¹HNMR (CDCl₃) δ: 1.46–1.64 (m, 2H); 2.14–2.32 (m, 2H); 2.53–2.78 (m, 2H); 3.30–4.49 (m, 2H); 4.49–4.68 (m, 2H); 3.83–4.01 (m, 1H); 5.13 (s, 2H); 7.30–7.43 (m, 5H).

(2) A solution of 321 mg of the compound (III-10) in 25 ml of methanol is hydrogenated over 200 mg of 10% Pd-C at room temperature under 5 atmospheric pressure. The mixture is filtered to remove the catalyst, and the filtrate is concentrated under reduced pressure to give 175 mg of the objective compound (Ia-8).

EXAMPLE 9

(1R*,5R*,6S*)-6-Acetylamino-3-azabicyclo[3,3,0]octane (Ia-9)

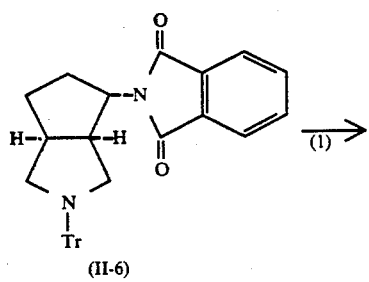

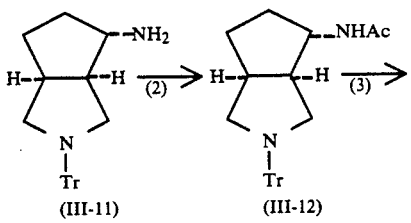

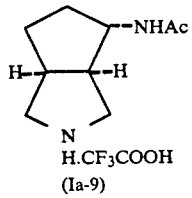

(1) A mixture of 2.15 g of the compound (II-6), 648 mg of hydrazine anhydrous, 70 ml of ethanol, and 70 ml of 1,4-dioxane is refluxed under heating for 49 hours. After cooling, the resulting precipitate is filtered off and the filtrate is concentrated under reduced pressure to give 1.55 g (Yield: 97%) of the objective amine (III-11).

(2) Without purification, the amine (III-11) is dissolved in 50 ml of methylene chloride. To the solution is added 638 mg of triethylamine and 495 mg of acetyl chloride, and the mixture is stirred at room temperature for 15 minutes. The reaction mixture is washed with aqueous NaHCO₃, dried over Na₂SO₄ and concentrated under reduced pressure. The residue is subjected to silica gel column chromatography, eluting with ethyl acetate to give 1.26 g (Yield: 73%) of the objective acetamide (III-12).

¹HNMR (CDCl₃) δ: 1.32–1.53 (m, 1H); 1.57–1.78 (m, 1H); 1.83–2.24 (m, 5H); 1.95 (s, 3H); 2.34–2.57 (m, 2H); 2.70–2.83 (m, 1H); 4.23–4.40 (m, 1H); 5.27–5.47 (m, 1H); 7.09–7.57 (m, 15H).

(3) A solution of 1.24 g of the acetamide (III-12) in 20 ml of aqueous CF₃COOH is stirred at room temperature for 10 minutes and then added excess water. The aqueous layer is washed with ethyl acetate and concentrated under reduced pressure. The residue is mixed with saturated aqueous NaOH and extracted with methylene chloride. The organic layer is dried over Na₂SO₄ and concentrated under reduced pressure to give 417 mg (Yield: 80%) of the objective amine (Ia-9).

¹HNMR (CD₃OD) δ: 1.22–1.61 (m, 2H); 1.84–2.06 (m, 2H); 1.91 (s, 3H); 2.29–2.46 (m, 1H); 2.54–2.97 (m, 5H); 3.73–3.87 (m, 1H).

EXAMPLE 10

(1R*,5S*)-1-Acetylaminomethyl-3-azabicyclo[3,3,0]octane (Ia-10)

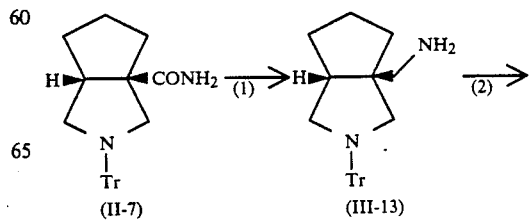

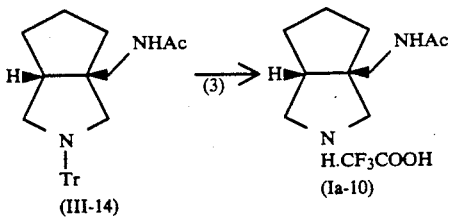

(1) To a solution of 1.2 g of the amide (II-7) in 50 ml of dry THF is added 360 mg of LiAlH$_4$, and the mixture is refluxed for 0.5 hour. The mixture is mixed with 0.7 ml of water under ice-cooling and filtered, and the filtrate is concentrated. The residue is dissolved in methylene chloride, dried over Na$_2$SO$_4$, and concentrated to give 930 mg of the objective compound (III-13) as an oil.

IR (film): 3350 cm$^{-1}$.

(2) To a solution of 930 mg of the amine (III-13) and 760 mg of Et$_3$N in 18 ml of dry methylene chloride is added a solution of 400 mg of CH$_3$COCl in 2 ml of methylene chloride under ice-cooling, and the mixture is stirred at room temperature for 10 minutes. The reaction mixture is mixed with aqueous NaHCO$_3$, and extracted with methylene chloride. The organic layer is washed with water, dried over Na$_2$SO$_4$ and concentrated under reduced pressure to give 930 mg of the objective compound (III-14) as an oil.

IR (film): 3280, 1650 cm$^{-1}$.

$^1$HNMR (CDCl$_3$) δ: 1.10–2.70 (m, 11H); 1.95 (s, 3H); 3.30 (d, J=6 Hz, 2H); 5.90 (brs, 1H); 7.10–7.58 (m, 15H).

(3) A solution of 930 mg of the amide (III-14) in 10 ml of aqueous CF$_3$COOH is heated on water bath. After cooling, the mixture is extracted with ethyl acetate, and the aqueous layer is concentrated under reduced pressure to give 470 mg of the compound (Ia-10) as an oil.

$^1$HNMR (CD$_3$OD) δ: 1.50–2.00 (m, 6H); 2.15 (s, 3H); 2.60–2.70 (m, 1H); 2.90–3.60 (m, 4H); 3.40 (s, 2H).

EXAMPLE 11

(1R*,5R*)-1-(N-formyl-N-methylaminomethyl)-3-azabicyclo[3,3,0]octane(Ia-11)

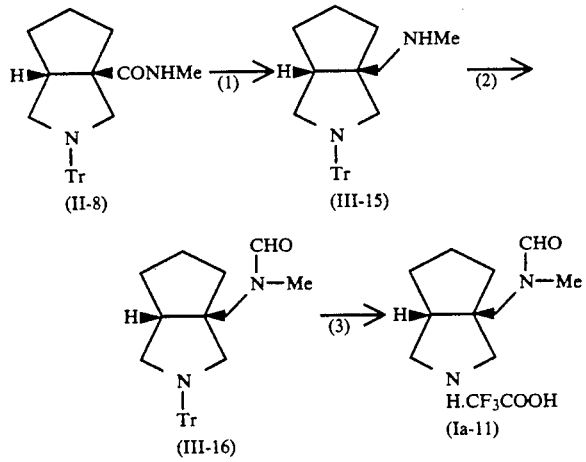

(1) To a solution of 1.3 g of the amide (II-8) in 50 ml of dry THF is added 370 mg of LiAlH$_4$, and the mixture is refulxed for 30 minutes. After cooling, the mixture is mixed with 0.7 ml of water and filtered. The filtrate is dried and concentrated to give 1.2 g of the objective compound (III-15) as an oil.

IR (film): 3400, 1590, 1485, 1450 cm$^{-1}$.

$^1$HNMR (CDCl$_3$) δ: 1.30–2.80 (m, 14H); 3.40–3.90 (m, 2H); 7.00–7.60 (m, 15H); 8.00 (brs, 1H).

(2) To a solution of 1.2 g of the compound (III-15) in 20 ml of dry methylene chloride are added 950 mg of Et$_3$N and 830 mg of acetic-formic anhydride under ice-cooling, and the mixture is allowed to stand at room temperature for 15 minutes. The reaction mixture is mixed with aqueous NaHCO$_3$ and extracted with methylene chloride. The organic layer is washed with water, dried over Na$_2$SO$_4$ and concentrated. The residue is chromatographed on a column of silica gel, eluting with ethyl acetate-n-hexane (1:1 v/v) to give 590 mg of the objective compound (III-16) as an oil.

IR (film): 1675, 1485, 1450 cm$^{-1}$.

$^1$HNMR (CDCl$_3$) δ: 1.45–2.40 (m, 1H); 2.83 (s, 3H); 3.14, 3.60 (d, d, J=9 Hz, J$_1$=9 Hz, 1H); 3.15, 3.29 (d, d, J=9 Hz, J$_1$=9 Hz, 1H); 7.16–7.50 (m, 15H); 8.03 (s, 1H).

(3) A solution of 590 mg of the compound (III-16) in 10 ml of aqueous CF$_3$COOH is heated at 50° C. for 5 minutes. After cooling, the mixture is extracted with ethyl acetate. The aqueous layer is concentrated under reduced pressure to give 400 mg of the objective compound (Ia-11) as an oil.

IR (film): 3420, 1660 cm$^{-1}$.

$^1$HNMR (CD$_3$OD) δ: 1.50–3.70 (m, 13H); 2.92 (s, 3H); 8.10 (s, 1H).

EXAMPLE 12

(1R*,5R*)-1-Ethoxycarbonylamino-3-azabicyclo[3,3,0]octane (Ia-12)

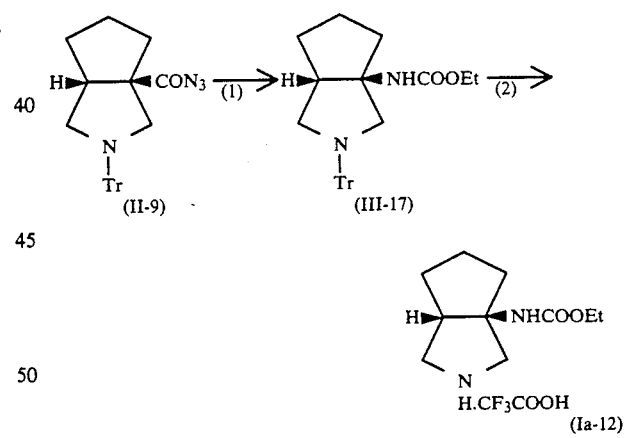

(1) A solution of 1.7 g of the compound (II-9) in 25 ml of ethanol is refluxed for 2 hours and concentrated. The residue is chromatographed on a column of silica gel, eluting with ethyl acetate-n-hexane (1:5 v/v) to give the objective compound (III-17) as an oil.

IR (film): 3320, 1710 cm$^{-1}$.

$^1$HNMR (CDCl$_3$) δ: 1.00–2.65 (m, 11H); 1.20 (t, J=7.5 Hz, 3H); 4.03 (q, J=7.5 Hz, 2H); 4.97 (s, 1H); 7.05–7.60 (m, 15H).

(2) A solution of 1.5 g of the compound (III-17) in 10 ml of aqueous CF$_3$COOH is heated on water bath. After cooling, the mixture is extracted with ether, and the aqueous layer is concentrated under reduced pressure to give 640 mg of the objective compound (Ia-12) as an oil.

IR (film): 3200, 1700 cm$^{-1}$.

$^1$HNMR (CD$_3$OD) δ: 1.24 (t, J=7.5 Hz, 3H); 1.50–2.10 (m, 6H); 2.75–2.95 (m, 2H); 3.15 (d, J=12.5 Hz, 1H); 3.69 (d, J=12.5 Hz, 1H); 3.70–3.80 (m, 1H); 4.10 (q, J=7.5 Hz, 2H).

EXAMPLE 13

(1R*,5R*)-1-(N-Formyl-N-ethylaminomethyl)-3-azabicyclo[3,3,0]octane (Ia-13)

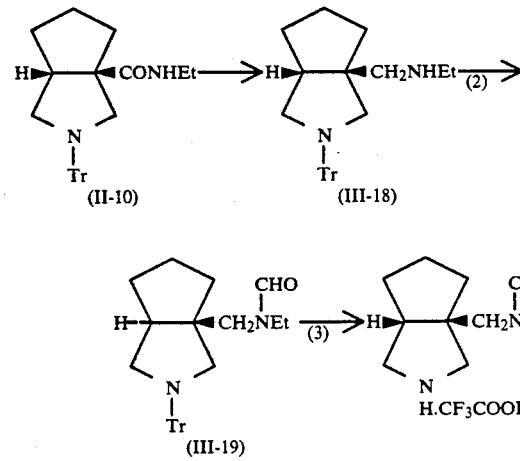

(1) To a solution of 2.25 g of the amide (II-10) in 50 ml of dry THF is added 600 mg of LiAlH$_4$, and the mixture is refluxed for 15 minutes. After cooling, the solution is mixed with 1.2 ml of water and filtered, and the filtrate is concentrated. The resulting residue is dissolved in methylene chloride, dried over Na$_2$SO$_4$ and concentrated under reduced pressure to give 2.0 g of the objective compound (III-18) as an oil.

IR (film): 3300, 1482, 1442 cm$^{-1}$.

(2) To a solution of 2.16 g of the amine (III-18) in 22 ml of dry methylene chloride are added 1.59 g of Et$_3$N and 700 mg of acetic-formic anhydride under ice-cooling, and the mixture is allowed to stand for 15 minutes. The mixture is mixed with aqueous NaHCO$_3$ and extracted with methylene chloride, and the organic layer is concentrated. The residue is chromatographed on a column of silica gel, eluting with ethyl acetate-n-hexane (1:2 v/v) to give 1.48 g of the objective compound (III-19) as an oil.

IR (film): 1660 cm$^{-1}$.

(3) A mixture of 1.38 g of the compound (III-19) in 13.8 ml of aqueous CF$_3$COOH is heated on water bath. After cooling, the mixture is washed with ethyl acetate, and the aqueous layer is concentrated under reduced pressure to give 790 mg of the compound (Ia-13) as an oil.

$^1$HNMR (CD$_3$OD) δ: 1.22 (t, J=7.5 Hz, 3H); 1.50–2.10 (m, 6H); 2.50–2.68 (m, 1H); 2.94–3.68 (m, 8H); 8.21 (s, 1H).

EXAMPLE 14

(1R*,2S*,6R*)-2-Amino-8-azabicyclo[4,3,0]nonane (Ia-14)

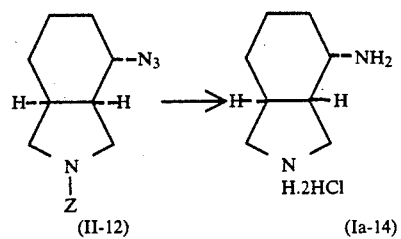

A solution of 360 mg of the azide (II-12) in 18 ml of methanol is hydrogenated over 360 mg of 10% Pd-C under 5 atomspheric pressure. The reaction mixture is filtered, and the filtrate is concentrated under reduced pressure to give 152 mg of an oil, which is treated with HCl-MeOH to give the compound (Ia-14) as crystals. mp. 265°–269° C.

IR (film): 3250, 2900, 1650 cm$^{-1}$.

IR (film): 3380, 3000, −2500, 1595, 1500 cm$^{-1}$.

EXAMPLE 15

(1R*, 2R*, 6S*)-2-(N-t-Butoxycarbonyl-N-methylamino)-8-azabicyclo[4,3,0]nonane (Ia-15)

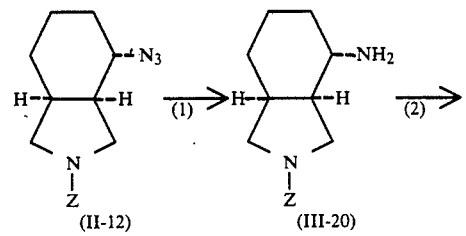

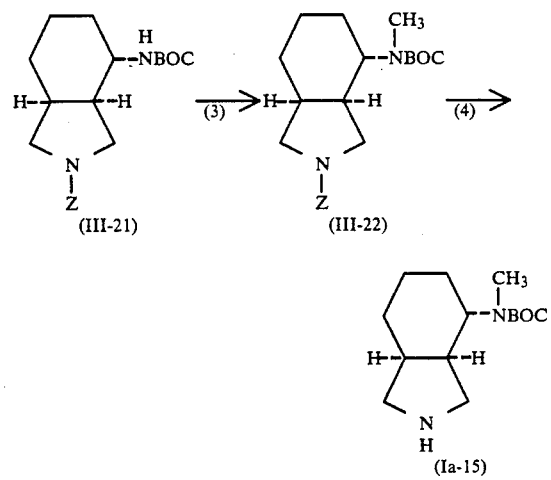

(1) A mixture of 608 mg of the compound (II-12), 637 mg of triphenylphosphine, 30 ml of THF, and 3 ml of water is heated at 60° C. for 4 hour with stirring, and then concentrated under reduced pressure. The residue is extracted with d-HCl, and the aqueous layer is washed with ether, basified with aqueous potassium carbonate and extracted with ether. The organic layer is washed with water, dried over MgSO$_4$ and concentrated under reduced pressure to give 444 mg (Yield: 80%) of the objective compound (III-20).

¹HNMR (CDCl₃) δ: 1.03–1.78 (m, 8H); 2.32–2.45 (m, 2H); 3.12–3.69 (m, 5H); 5.11 (d, 1H, J=13 Hz); 5.15 (d, 1H, J=13 Hz); 7.24–7.74 (m, 5H).

(2) To a solution of 440 mg of the compound (III-20) in 20 ml of methylene chloride is added 422 mg of di-tert-butyl dicarbonate. The mixture is allowed to stand at room temperature for 15 hours, and chromatographed on a column of silica gel, eluting with toluene-ethyl acetate (4:1 v/v) to give 387 mg (Yield: 64%) of the compound (III-21).

¹HNMR (CDCl₃) δ: 1.09–1.38 (m, 1H); 1.44 (s, 9H); 1.48–1.68 (m, 4H); 1.80–2.06 (m, 2H); 2.30–2.54 (m, 1H); 3.18–3.63 (m, 5H); 4.30–4.48 (m, 1H); 5.02–5.23 (m, 2H); 7.15–7.43 (m, 5H).

(3) To a solution of 380 mg of the compound (III-21) in 10 ml of DMF are added 45 mg of 60% sodium hydride and 158 mg of methyl iodide, and the mixture is stirred with heating at 60° C. for 1 hour. The reaction mixture is poured into ice water, and the mixture is extracted with ether. The ether layer is washed water, dried over MgSO₄ and concentrated under reduced pressure. The residue is chromatographed on a column of silica gel, eluting with toluene-ethyl acetate (1/1 v/v) to give 381 mg (Yield: 97%) of the compound (III-22).

¹HNMR (CDCl₃) δ: 1.27–1.78 (m, 15H); 2.02–2.28 (m, 1H); 2.46–2.70 (m, 4H); 3.17–3.58 (m, 4H); 3.67–4.00 (m, 1H); 4.99–5.27 (m, 2H); 7.13–7.57 (m, 5H).

(4) A solution of 375 mg of the compound (III-22) in 30 ml of methanol is hydrogenated over 200 mg of 10% of Pd-C under atmospheric pressure at room temperature. After the catalyst are filtered off, the filtrate is concentrated under reduced pressure to give 226 mg (Yield: 92%) of the objective compound (Ia-15).

¹HNMR (CDCl₃) δ: 1.22–1.74 (m, 14H); 1.87–2.60 (m, 4H); 2.67–3.01 (m, 7H); 3.86–4.06 (m, 1H).

EXAMPLE 16

(1R*,2R*,6S*)-2-Formylamino-8-azabicyclo[4,3,0]nonane (Ia-16)

(1R*,2S*,6S*)-2-Formylamino-8-azabicyclo[4,3,0]nonane (Ia-17)

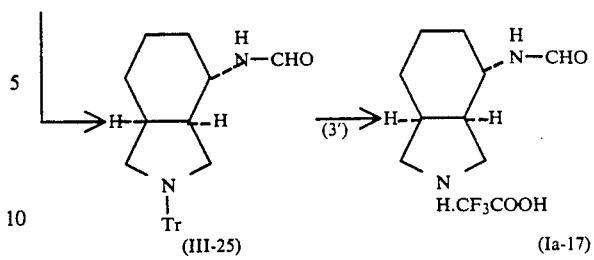

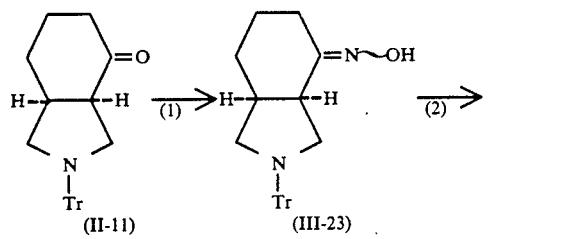

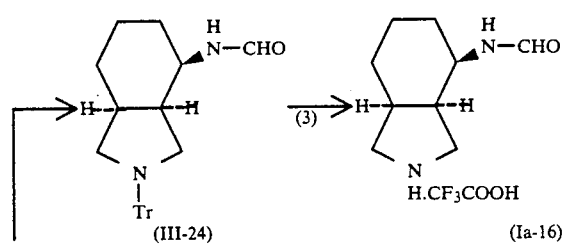

(1) A solution of 6.5 g of the compound (II-11) in 65 ml of methylene chloride are added 1.76 g of NH₂OH.HCl and 65 ml of 10% NaOH, and the mixture is heated at 50° C. for 30 minutes. The mixture is concentrated, and the residue is mixed with water and extracted with methylene chloride. The organic layer is washed with water, dried over Na₂SO₄ and concentrated to give 6.6 g of the compound (III-23).

¹HNMR (CDCl₃) δ: 1.0–1.80 (m, 4H); 1.90–3.10 (m, 8H); 7.05–7.67 (m, 15H).

IR (CHCl₃): 3560–3100, 890 cm⁻¹.

(2) To a solution of 1.72 g of LiAlH₄ in 172 ml of dry THF is added a solution of 9 g of the compound (III-23) in 90 ml of dry THF, and the mixture is refluxed for 30 minutes. The mixture is mixed with 36.3 ml of aqueous THF under ice-cooling and filtered, and the filtrate is concentrated to give 8.35 g of the amine. It is dissolved in 83.5 ml of dry methylene chloride, and the mixture is mixed with 6.6 g of Et₃N and 3.84 g of acetic-formic anhydride under ice-cooling and stirred at room temperature for 30 minutes. The solution is mixed with water and extracted with methylene chloride. The organic layer is washed with water, dried over Na₂SO₄ and concentrated. The residue is chromatographed on a column of silica gel, eluting with n-hexane-ethyl acetate (1:1 v/v) to give 3.6 g of the compound (III-24) and 1.0 g of the compound (III-25).

Compound (III-24): mp. 166°–167° C.

¹HNMR (CDCl₃) δ: 1.07–2.38 (m, 8H); 2.50–2.96 (m, 4H); 3.88–4.31 (m, 1H); 5.20–5.60 (m, 1H); 7.01–7.67 (m, 15H); 8.05 (s, 1H).

IR (Nujol): 3230, 1650, 710 cm¹.

Compound (III-25): mp. 235°–236° C.

¹HNMR (CDCl₃) δ: 1.25–2.13 (m, 6H); 2.15–2.45 (m, 2H); 2.5–3.0 (m, 4H); 3.98 0.3 (m, 1H); 5.05–5.38 (m, 1H); 6.98–7.65 (m, 15H); 8.13 (s, 1H).

IR (Nujol: 3250, 1640, 690 cm¹.

(3) A solution of 1.1 g of the compound (III-24) in 10 ml of aqueous CF₃COOH is stirred under ice-cooling for 5 minutes and washed with ethyl acetate. The aqueous layer is concentrated to give 750 mg of the compound (Ia-16). mp. 127°–130° C.

¹HNMR (CD₃OD) δ: 2.35–2.52 (m, 1H); 2.79–2.98 (m, 1H); 3.10–3.40 (m, 5H); 4.15–4.28 (m, 1H); 8.09 (s, 1H).

IR (Nujol): 3225, 1690, 1640 cm⁻¹.

(3') A solution of 850 mg of the compound (III-25) in 8 ml of aqueous CF₃COOH is stirred under ice-cooling for 5 minutes and washed with ethyl acetate. The aqueous layer is concentrated to give 580 mg of the compound (Ia-17). mp. 230°–232° C.

¹HNMR (CD₃OD) δ: 1.20–1.78 (m, 5H); 1.80–1.90 (m, 1H); 2.10–2.26 (m, 1H); 2.51–2.70 (m, 1H); 3.10–3.40 (m, 5H); 3.68–3.81 (m, 1H); 8.08 (s, 1H).

IR (Nujol): 3250, 1675, 1650 cm⁻¹.

EXAMPLE 17

(1R*,2S*,6S*)-2-(N-Methylformylamino)-8-azabicyclo[4,3,0]-nonane (Ia-18)

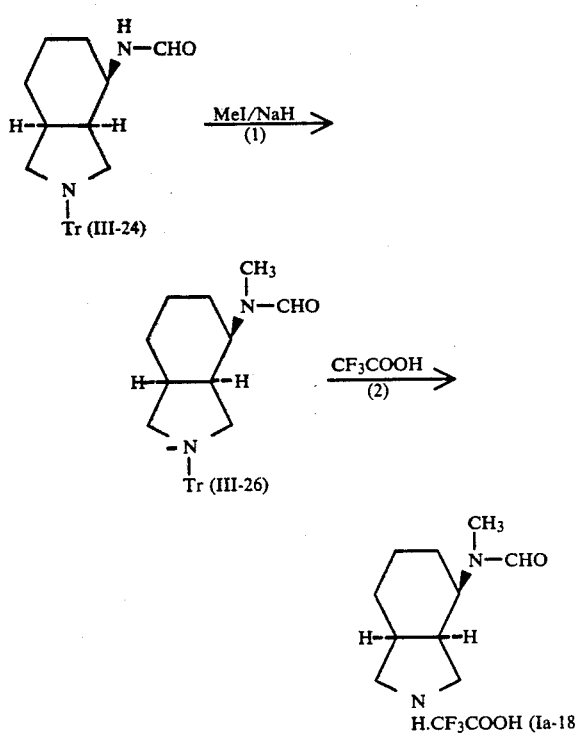

(1) To a solution of 1.0 g of the compound (III-24) in 10 ml of dry DMF are added 415 mg of 60% NaH and 117 mg of MeI under ice-cooling, and the mixture is stirred at room temperature for 30 minutes. The mixture is mixed with ice-water and extracted with ethyl ether. The organic layer is washed with water, dried over MgSO₄ and concentrated to give 1.1 g of the compound (III-26).

¹HNMR (CD₃OD) δ: 0.70–2.18 (m, 8H); 2.25 (s, 3H); 2.91 (s); 2.50–3.10 (m, 4H); 3.18–3.51 (m, 1H); 7.10–7.67 (m, 15H); 8.00 (s, 1H); 8.02 (s)

IR (CHCl₃): 1660, 900 cm⁻¹.

(2) A solution of 1.1 g of the compound (III-26) in 10 ml of aqueous CF₃COOH is stirred under ice-cooling for 5 minutes. The reaction mixture is washed with ethyl ether, and the aqueous layer is concentrated to give 660 mg of the compound (Ia-18).

IR (Nujol): 1780, 1680, 1640 cm⁻¹.

EXAMPLE 18

(1R*,2S*,6S*)-2-Amino-8-azabicyclo[4,3,0]nonane (Ia-19)

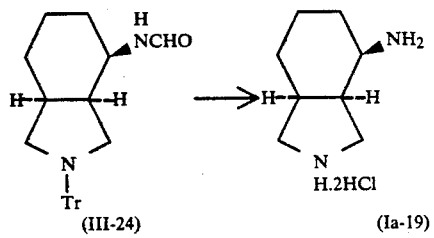

A mixture of 570 mg of the compound (III-24) in 10 ml of c. HCl is heated at 130° C. for 1 hour and washed with ethyl acetate. The aqueous layer is concentrated under reduced pressure to give 258 mg of the compound (Ia-19). mp. 280°–285° C.

¹HNMR (DMSO) δ: 1.13–1.55 (m, 3H); 1.65–1.83 (m, 2H); 2.22–2.43 (m, 1H); 2.58–2.58 (m, 1H); 2.93–3.03 (m, 1H); 3.04–3.25 (m, 3H); 3.33–3.50 (m, 1H); 8.42 (bs, 3H); 9.70 (bs, 1H); 9.82 (broad s, 1H).

IR (Nujol): 3375, 3300, 1500 cm⁻¹.

EXAMPLE 19

(1R*,2S*,7R*)-2-Formylamino-9-azabicyclo[5,3,0]decane (Ia-20)

(1R*,2R*,7R*)-2-Formylamino-9-azabicyclo[5,3,0]decane (Ia-21)

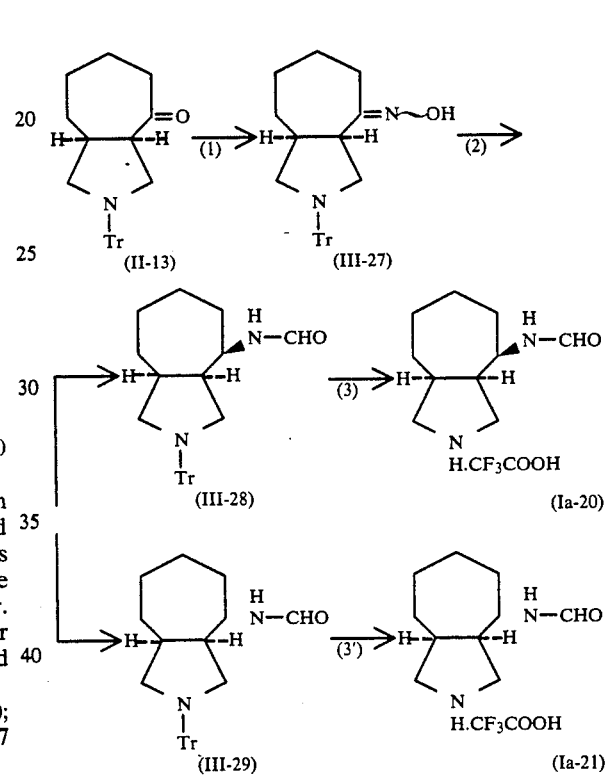

(1) To a solution of 3.1 g of the compound (II-13) in 31 ml of methylene chloride is added a mixture of 1.08 g of NH₂OH·HCl, 9.5 ml of 10% NaOH and 50 ml of methanol, and the mixture is heated at 80° C. for 30 minutes and concentrated. The resulting residue is mixed with ice water and concentrated. The residue is mixed with ice water and extracted with methylene chloride. The organic layer is washed with water, dried over Na₂SO₄ and concentrated to give 3.1 g of the compound (III-27).

¹HNMR (CDCl₃) δ: 0.9–1.95 (m, 10H); 2.10–3.20 (m, 4H); 7.05–7.60 (m, 15H).

IR (film): 3600, 3150 cm⁻¹.

(2) To a solution of 1.29 g of LiAlH₄ in 70 ml of dry THF is added a solution of 3.5 g of the compound (III-27) in 35 ml of dry THF, and the mixture is refluxed for 4.5 hours. The solution is gradually mixed with 27.5 ml of aqueous THF under ice-cooling and filtered. The filtrate is concentrated to give 3.05 g of the amine, which is dissolved in 30 ml of dry methylene chloride. The mixture is mixed with 2.34 g of Et₃N and 1.36 g of acetic-formic anhydride under ice-cooling, and stirred at room temperature for 30 minutes. The mixture is mixed with ice-water and extracted with methylene chloride. The organic layer is washed with water, dried over Na$_2$SO$_4$ and concentrated. The residue is chromatographed on a column of silica gel, eluting with n-hexane-ethyl acetate (1:1 v/v) to give 1.7 g of the compound (III-28) and 200 mg of the compound (III-29).

Compound (III-28).

$^1$HNMR (CDCl$_3$) δ: 1.10–1.30 (m, 2H); 1.35–1.96 (m, 8H); 2.20–2.40 (m, 1H); 2.80–3.20 (m, 2H); 3.65–3.85 (m, 1H); 5.30–5.48 (m, 1H); 7.10–7.55 (m, 15H); 7.99, 8.01 (each s, 1H).

IR (Nujol): 3275, 1650 cm$^{-1}$.

Compound (III-29)

$^1$HNMR (CDCl$_3$) δ: 1.10–1.50 (m, 6H); 1.65–1.85 (2H); 1.90–2.02 (m, 2H); 2.35–2.65 (m, 2H); 2.70–3.00 (m, 2H); 4.15–4.35 (m, 1H); 7.95, 8.37 (each s, 1H).

IR (CHCl$_3$): 1670, 900 cm$^{-1}$.

(3) A solution of 800 mg of the compound (III-28) in 8 ml of aqueous CF$_3$COOH is stirred under ice-cooling for 5 minutes and washed with ethyl acetate. The aqueous layer is concentrated to give 535 mg of the compound (Ia-20).

$^1$HNMR (CD$_3$OD) δ: 1.25–2.00 (m, 8H); 2.45–2.70 (m, 2H); 2.85–3.15 (m, 2H); 3.40–3.64 (m, 2H); 3.90–4.10 (m, 1H); 8.01, 8.10 (each s, 1H).

(3') A solution of 200 mg of the compound (III-29) in 2 ml of aqueous CF$_3$COOH is stirred under ice-cooling for 5 minutes and washed with ethyl acetate. The aqueous layer is concentrated to give 130 mg of the compound (Ia-21).

$^1$HNMR (CD$_3$OD) δ: 1.35–2.00 (m, 7H); 2.47–2.70 (m, 1H); 2.73–3.03 (m, 2H); 3.06–3.25 (m, 1H); 3.36–3.60 (m, 3H); 4.30–4.45 (m, 1H); 8.10, 8.13 (each s, 1H).

IR (film): 1770, 1670 cm$^{-1}$.

EXAMPLE 20

(1R*,2S*,7R*)-2-Amino-9-azabicyclo[5,3,0]decane (Ia-22)

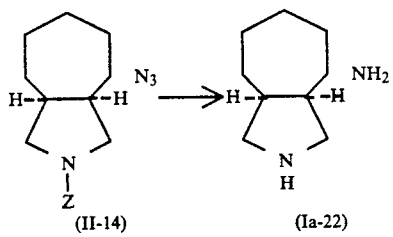

A solution of 450 mg of the compound (II-14) in 20 ml of methanol is hydrogenated over 450 mg of 10% Pd-C under 5 atmospheric pressure to give 200 mg of the objective compound (Ia-22).

IR (film): 3250, 1550, 1422 cm$^{-1}$.

$^1$HNMR (CDCl$_3$) δ: 1.20–2.00 (m, 10H); 2.30–3.80 (m, 5H).

EXAMPLE 21

(1R*,2S*,7R*)-2-(t-Butoxycarbonylamino)-9-azabicyclo[5,3,0]decane (Ia-23)

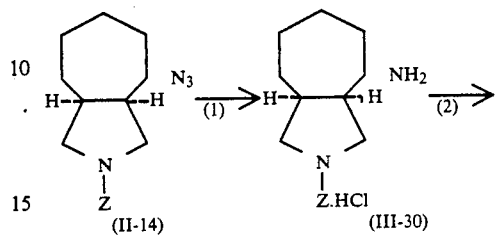

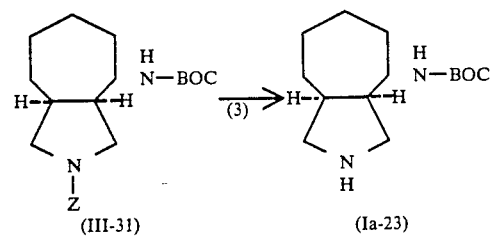

(1) A mixture of 800 mg of the compound (II-14), 30 ml of THF, 3 ml of water and 908 mg of Ph$_3$P is heated at 120° C. for 2 hours and concentrated. The resulting residue is mixed with 6N.HCl and filtered. The filtrate is washed with ethyl acetate and evaported under reduced pressure to give 730 mg of the compound (III-30).

$^1$HNMR (CD$_3$OD) δ: 1.25–2.25 (m, 9H); 2.95–3.32 (m, 4H); 3.67–3.97 (m, 2H); 5.11 (s, 2H); 7.32–7.38 (m, 5H).

IR (Nujol): 3100–2600, 1685, 1150 cm$^{-1}$.

(2) To a solution of 720 mg of the compound (III-30) in 30 ml of methylene chloride are added 227 mg of Et$_3$N and 645 mg of di-tert-butyl dicarbonate, and the mixture is heated at 50° C. for 1 hour and concentrated. The residue is chromatographed on a column of silica gel, eluting with methylene chloride~2% methanol-methylene chloride to give 820 mg of the compound (III-31).

$^1$HNMR (CD$_3$OD) δ: 1.45 (s, 9H); 1.20–2.15 (m, 10H); 2.92–3.05 (m, 1H); 3.15–3.30 (m, 1H); 3.52 (bs, 1H); 3.65–3.90 (m, 2H); 4.45 (bs, 1H); 5.12 (s, 2H); 7.32–7.38 (m, 5H).

IR (Nujol): 3365, 1705, 1680, 1160 cm$^{-1}$.

(3) A solution of 400 mg of the compound (III-31) in 30 ml of methanol is hydrogenated over 200 mg of 10% Pd-C. After removal of the catalyst, the filtrate is concentrated to give 250 mg of the compound (Ia-23).

$^1$HNMR (CDCl$_3$) δ: 1.44 (s, 9H); 1.10–2.00 (m, 10H); 2.45–2.60 (m, 1H); 2.75–2.90 (m, 1H); 3.10–3.27 (m, 2H); 3.40–3.65 (m, 1H); 4.49 (bs, 1H).

IR (CHCl$_3$): 3420, 1695, 1160 cm$^{-1}$.

EXAMPLE 22

(1R*,2S*,7R*)-2-(N-Methyl-t-butoxycarbonylamino)-9-azabicyclo[5,3,0]decane (Ia-24)

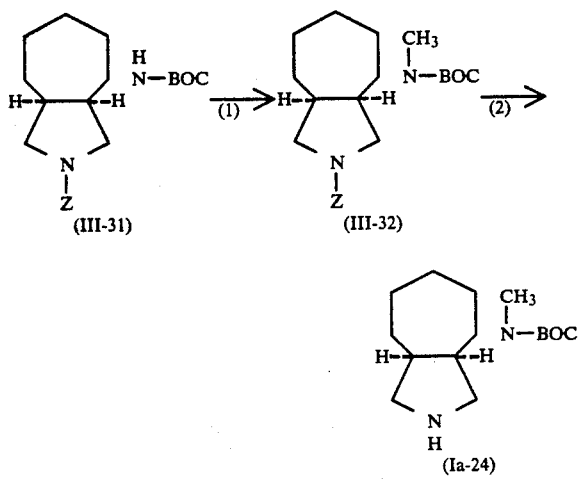

(1) To a solution of 400 mg of the compound (III-31) in 4 ml of dry DMF are added 49 mg of 60% NaH and 175 mg of MeI under ice-cooling, and the mixture is stirred at room temperature for 30 minutes. The mixture is mixed with ice water and extracted with ethyl ether. The organic layer is washed with water, dried over MgSO$_4$ and concentrated to give 410 mg of the compound (III-32).

$^1$HNMR (CDCl$_3$) δ: 1.44 (s, 9H); 1.20–2.25 (m, 9H); 2.70–2.83 (m, 3H); 2.88–3.40 (m, 3H); 3.45–4.15 (m, 3H); 5.11 (s, 2H); 7.32–7.38 (m, 5H).

IR (film): 1680, 1130 cm$^{-1}$.

(2) A solution of 410 mg of the compound (III-32) in 20 ml of methanol is hydrogenated over 200 mg of 10% Pd-C. After removal of the catalyst, the filtrate is concentrated to give 270 mg of the compound (Ia-24).

$^1$HNMR (CDCl$_3$) δ: 1.45 (s, 9H); 1.20–2.40 (m, 10H); 2.65–3.00 (4H); 3.15–4.10 (m, 5H).

IR (CHCl$_3$): 1670, 1140 cm$^{-1}$.

EXAMPLE 23

(1R*,2S*,7R*)-2-(N-Methylformylamino)-9-azabicyclo[5,3,0]decane (Ia-25)

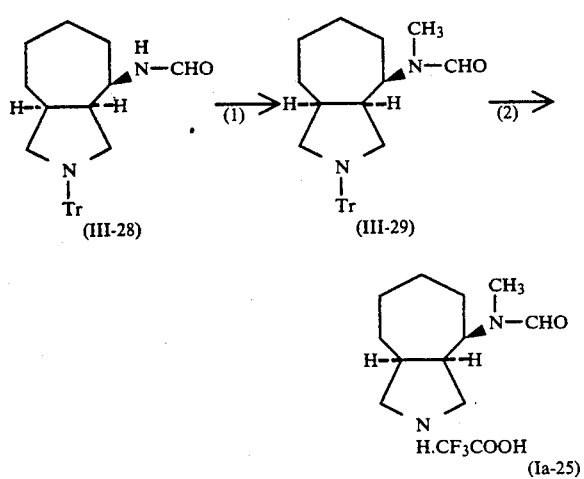

(1) To a solution of 600 mg of the compound (III-28) in 3 ml of dry DMF are added 68 mg of 60% NaH and 240 mg of CH$_3$I under ice-cooling, and the mixture is stirred at room temperature for 30 minutes. The mixture is mixed with ice water, and extracted with ethyl ether. The organic layer is washed with water, dried over MgSO$_4$ and concentrated to give 650 mg of the compound (III-29).

$^1$HNMR (CDCl$_3$) δ: 1.10–1.90 (m, 10H); 2.20–2.45 (m, 1H); 2.50–2.64 (m, 1H); 2.71 (s, 3H); 2.74 (s); 2.65–2.83 (1H); 2.85–3.20 (m, 2H); 7.08–7.53 (m, 15H); 7.85, 7.88 (each s, 1H).

(2) A solution of 650 mg of the compound (III-29) in 8 ml of aqueous CF$_3$COOH is stirred under ice-cooling for 5 minutes and washed with ethyl acetate. The aqueous layer is concentrated to give 450 mg of the compound (Ia-25).

$^1$HNMR (CD$_3$OD) δ: 1.25–2.00 (m, 7H); 2.40–2.65 (m, 1H); 2.278 (s, 3H); 2.91 (s); 2.75–3.03 (m, 3H); 3.25–3.43 (m, 1H); 3.80–7.52 (m, 3H); 4.35–4.80 (m); 7.99, 8.15 (each s, 1H).

EXAMPLE 24

4-Aminooctahydroindole (Ia-26)

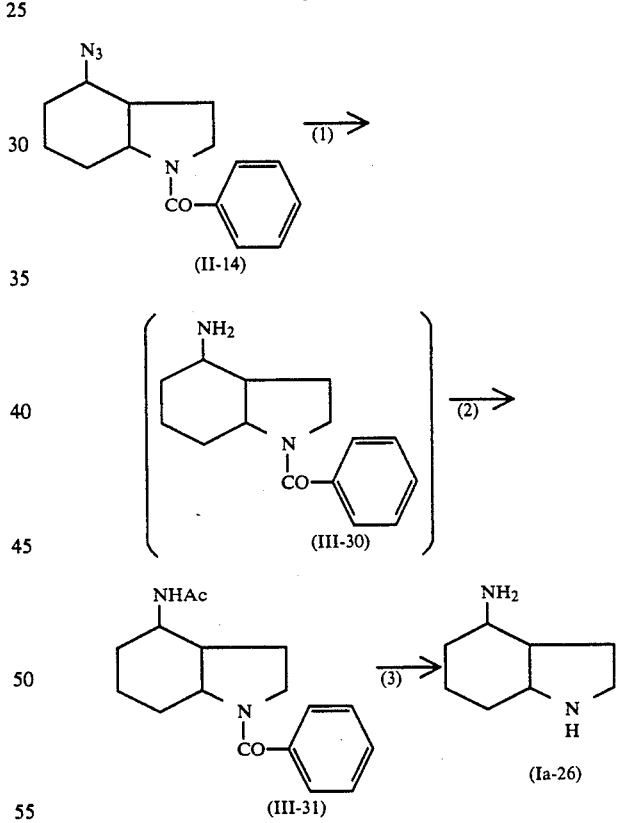

(1) A solution of 1.3 g of the compound (II-14) in 30 ml of methanol is hydrogenated over 800 mg of 10% Pd-C. After removal of the catalyst, the filtrate is concentrated under reduced pressure to give the compound (III-30) as an oil.

(2) A solution of the compound (III-30) in 20 ml of acetic anhydride is heated on water bath for 10 minutes and concentrated. The residue is mixed with aqueous NaHCO$_3$ and extracted with methylene chloride. The organic layer is washed with water, dried over Na$_2$SO$_4$, and concentrated. The residue is chromatographed on a column of silica gel, eluting with 10% methanol-ethyl acetate to give 540 mg of the compound (III-31) as an oil.

IR (film): 3270, 1610, 1540, 1425, 785 cm$^{-1}$.

$^1$HNMR (CDCl$_3$) δ: 1.20–2.30 (m, 9H); 3.30–3.50 (m, 4H); 6.10 (brs, 11H).

(3) A solution of 530 mg of the compound (III-31) in 20 ml of c-HCl is refluxed at 130° C. for 11 hours. After cooling, the mixture is filtered to remove the resulting benzoic acid, and the filtrate is concentrated under reduced pressure. The residue is mixed with aqueous Na$_2$CO$_3$ and extracted with methanol-methylene chloride (1/1 v/v). The aqueous layer is concentrated to give 109 mg of the objective compound (Ia-26) as an oil.

IR (film): 3350, 1595 cm$^{-1}$.

$^1$HNMR (CDCl$_3$) δ: 1.00–2.00 (m, 12H); 2.42–2.60 (m, 1H); 2.90–3.20 (m, 3H).

REFERENCE EXAMPLE 1

(1R*,5R*,6S*)-N-Trityl-6-oxo-3-azabicyclo[3,3,0]octane (II-1)

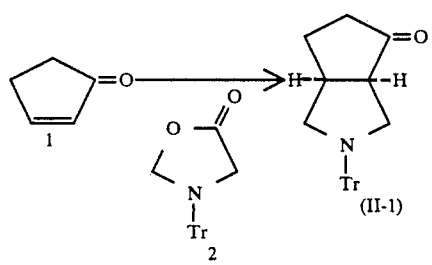

A solution of 2.1 g of cyclopentenone 1 and 9.2 g of 3-triphenylmethyl-5-oxazolidinone 2 [Bull. Chem. Soc. Jpn., 60 4079–4089 (1987)] in 100 ml of toluene is refluxed for 41 hours and concentrated. The residue is chromatographed on a column of silica gel, eluting with ethyl acetate-n.hexane (1:5 v/v) to give a residue, which is recrystallized from isopropyl ether to give 5 g (Yield: 55%) of the compound (II-1) as crystals. mp. 157°–158° C.

IR (Nujol): 1735 cm$^{-1}$.

$^1$HNMR (CDCl$_3$) δ: 1.55–3.30 (m, 10H); 7.05–7.49 (m, 15H).

REFERENCE EXAMPLE 2

(1R*,5S*,6S*)-5,6-Epoxy-3-azabicyclo[3,3,0]octane (II-2) and (1R*,5R*,6R*)-5,6-Epoxy-3-azabicyclo[3,3,0]octane (II-3)

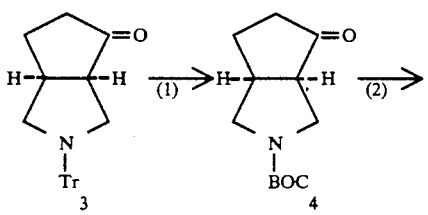

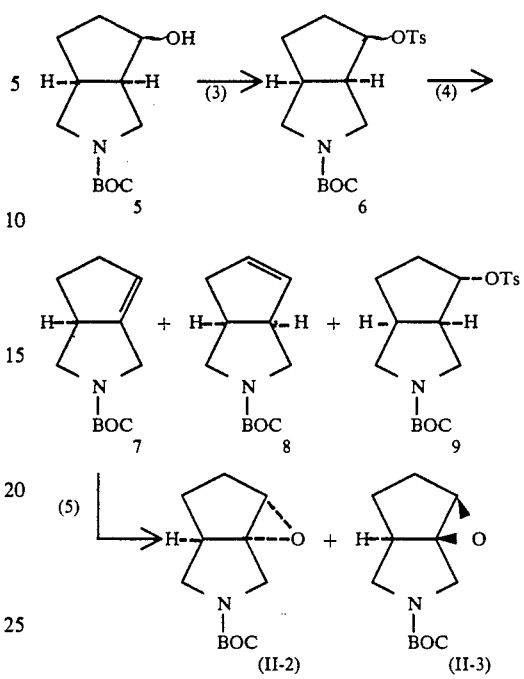

(1) A solution of 3 g of 7-oxo-3-trityl-3-azabicyclo[3,3,0]octane 3 in 30 ml of aqueous CF$_3$COOH is stirred at room temperature for 5 minutes. The mixture is poured into excess water, and the aqueous layer is washed with ethyl acetate and concentrated. The residue is dissolved in 50 ml of methylene chloride, and the solution is mixed with 1.24 g (12 mmol) of Et$_3$N and 2.67 g (11 mmol) of di-tert-butyl dicarbonate and stirred at room temperature for 5 minutes. The organic layer is washed with water, dried over Na$_2$SO$_4$ and concentrated. The residue is chromatographed on a column of silica gel, eluting with toluene-ethyl acetate (3:1 v/v) to give 1.5 g (Yield: 82%) of 7-oxo-3-tert-butyloxycarbonyl-3-azabicyclo[3,3,0]octane 4.

$^1$HNMR (CDCl$_3$) δ: 1.45 (s, 9H); 1.75–1.96 (m, 1H); 2.07–2.28 (m, 1H); 2.32–2.43 (m, 2H); 2.68–2.79 (m, 1H); 2.94–3.20 (m, 2H); 3.44–4.74 (m, 3H).

(2) To a solution of 1.5 g of the ketone 4 in 15 ml of ethanol is added 504 mg of NaBH$_4$, and the mixture is stirred at room temperature for 1 hour. The mixture is mixed with acetic acid and water, and the solution is extracted with ether. The ether layer is washed with water, dried over MgSO$_4$ and concentrated. The residue is chromatographed on a column of silica gel, eluting with toluene-ethyl acetate (1:1 v/v) to give 1.51 g (Yield: 100%) of the objective compound 5.

$^1$HNMR (CDCl$_3$) δ: 1.46 (s, 9H); 1.53–2.18 (m, 4H); 1.65 (s, 1H, OH); 2.48–2.90 (m, 2H); 3.10–3.68 (m, 4H); 4.05–4.15 (m, 0.2H*$^1$); 4.22–4.33 (m, 0.8H*$^2$).

*$^1$: CH—O of α-isomer
*$^2$: CH—O of β-isomer (3) To a solution of 1.51 g (6.6 mmol) of the alcohol 5 in 15 ml of dry pyridine is added 1.39 g (7.3 mmol) of p-toluenesulfonyl chloride, and the mixture is allowed to stand at room temperature for 66 hours. The mixture is concentrated, and the resulting residue is mixed with ice water and sodium hydrogencarbonate and extracted with methylene chloride. The methylene chloride layer is washed with water, dried over Na$_2$SO$_4$ and concentrated. The residue is chromatographed on a column of silica gel, eluting with toluene-ethyl acetate (4:1 v/v) to give 2.18 g (Yield: 94%) of the tosylate 6.

¹HNMR (CDCl₃) δ: 1.43 (s, 1.8H*³); 1.45 (s, 7.2H*⁴); 1.50–1.66 (m, 1H); 1.70–2.15 (m, 3H); 2.45 (s, 3H); 2.50–2.84 (m, 2H); 3.00–3.58 (m, 4H); 4.64–4.72 (m, 0.2H*⁵); 4.82–4.96 (m, 0.8H*⁵); 7.34 (d, 2H); 7.79 (d, 2H).

*³: t-Butyl protons of α-tosyl isomer
*⁴: t-Butyl protons of β-tosyl isomer
*⁵: CH—O of α-isomer
*⁶: CH—O of β-isomer (4) To a solution of 2.18 g of the tosylate 6 in 22 ml of dry DMSO is added 770 mg of potassium t-butoxide and the mixture is stirred at room temperature for 1 hour. The reaction mixture is mixed with ice water and extracted with ether. The ether layer is washed with water, dried over MgSO₄ and concentrated. The residue is chromatographed on a column of silica gel, eluting with toluene-ethyl acetate (10/1 v/v) to give 885 mg (Yield: 68%) of the compound 7, 163 mg (Yield: 12%) of the compound 8 as a by-product, and 77 mg (Yield: 4%) of the starting material 9.

compound 7.

¹HNMR (CDCl₃) δ: 1.20–1.66 (m, 1H); 1.46 (s, 9H); 2.05–2.26 (m, 1H); 2.47–2.80 (m, 3H); 3.04–3.28 (m, 1H); 3.72–3.98 (m, 3H); 5.45–5.56 (m, 1H).

(5) To a solution of 870 mg (4.2 mmol) of the olefin 7 in 30 ml of chloroform is added 947 mg (4.4 mmol) of 80% m-chloroperbenzoic acid under ice-cooling, and the mixture is stirred for 2 hours under ice-cooling. The reaction mixture is washed with aqueous NaHCO₃ and water, dried and concentrated. The residue is chromatographed on a column of silica gel, eluting with toluene-ethyl acetate (17/3 v/v) to give 433 mg (Yield: 46%) of the epoxide (II-2) and 459 mg (Yield: 49 %) of the compound (II-3).

Compound (II-2):

¹HNMR (CDCl₃) δ: 1.47 (s, 9H); 1.52–2.14 (m, 4H); 2.45–2.68 (m, 1H); 2.88 (q, 1H, J=11 Hz); 3.37–3.88 (m, 4H).

Compound (II-3):

¹HNMR (CDCl₃) δ: 1.07–1.28 (m, 1H); 1.40–1.58 (m, 1H); 1.46 (s, 9H); 1.76–1.94 (m, 1H); 2.18–2.40 (m, 2H); 3.04 (dd, 1H, J=10, 11.4 Hz); 3.45 (dd, 1H, J=10.2, 12.2 Hz); 3.64–3.88 (m, 3H).

REFERENCE EXAMPLE 3

(1R*,5R*,6S*)-N-Benzyloxycarbonyl-6-chloro-3-azabicyclo[3,3,0]octane (II-4)

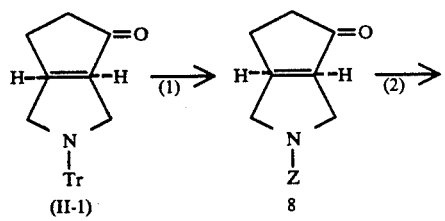

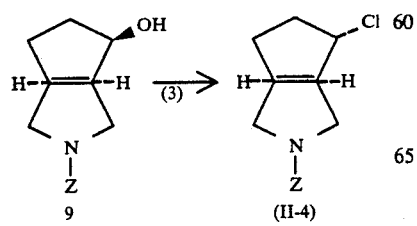

(1) A solution of 10.2 g of the ketone (II-1) in 40 ml of aqueous CF₃COOH is stirred at room temperature for 5 minutes. The solution is mixed with excess water, and the aqueous layer is washed with ethyl acetate. The aqueous layer is mixed with 20 g of sodium carbonate and 5.2 g of benzyl chloroformate, and the mixture is stirred at room temperature for 30 minutes. The mixture is extracted with ether, and the ether layer is washed with water, dried over MgSO₄ and concentrated to give 5.66 g (Yield: 79%) of the objective compound 8.

(2) To a solution of 4.28 g of the ketone 8 in 43 ml of anhydrous THF is added "L-Selectride®" (1M in THF, 25 ml) at −78°–−70° C. under nitrogen atmosphere. The mixture is stirred at the same temperature for 10 minutes, and then stirred further at room temperature for 16 hours. The reaction mixture is mixed with 3 ml of water under ice-cooling and mixed with 11 ml of 31% hydrogen peroxide at below 40° C., and the mixture is stirred at room temperature for 30 minutes. The solution is mixed with ice water and extracted with ether. The ether layer is washed with water, dried over MgSO₄ and concentrated to give 3.92 g (Yield: 91%) of the objective compound 9.

(3) A solution of 3.90 g (14.9 mmol) of the compound 9 and 5.87 g (22.4 mmol) of triphenylphosphine in 25 ml of carbon tetrachloride is refluxed for 1.5 hours. The mixture is chromatographed on a column of silica gel, eluting with toluene-ethyl acetate (5/1 v/v) to give 3.43 g (Yield: 82%) of the objective compound (II-4).

REFERENCE EXAMPLE 4

(1R*,5S*,7R*)-N-Benzyloxycarbonyl-7-mesyloxy-3-azabicyclo[3,3,0]octane (II-5)

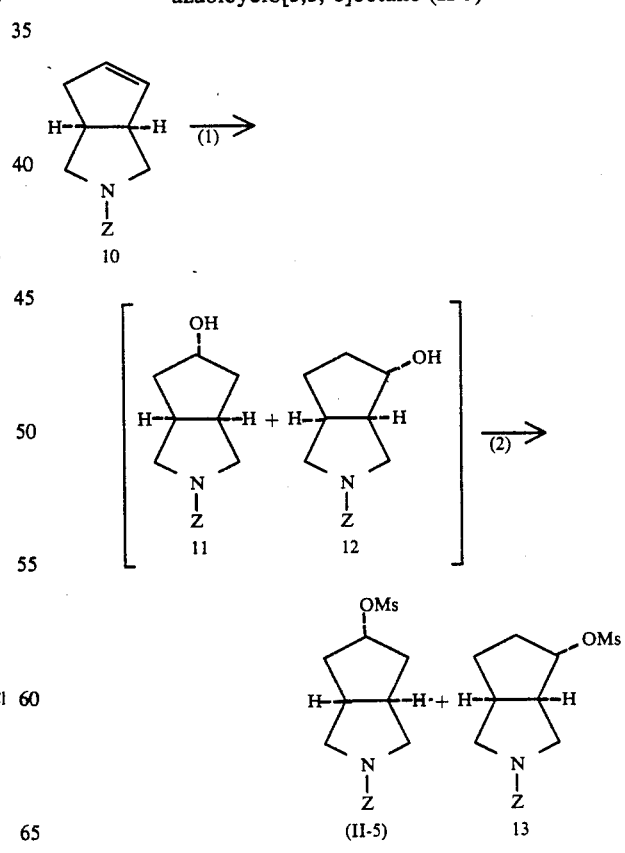

(1) To a solution of 500 mg of the olefin 10 in 10 ml of THF is added 9-borabicyclo[3,3,1]nonane (0.5M in THF, 4.5 ml), and the mixture is refluxed for 1 hour. The reaction mixture is cooled to room temperature and mixed with 1.2 ml of ethanol, 0.4 ml of 6N NaOH, and 0.8 ml of 30% aqueous hydrogen peroxide. The mixture is stirred at 50° C. for 30 minutes. This solution is mixed with excess aqueous potassium carbonate, and the supernatant is dried over MgSO4 and concentrated. The residue is chromatographed on a column of silica gel, eluting with toluene-ethyl acetate (1/1 v/v) to give 525 mg (Yield: 98%) of a mixture of alcohols 11 and 12.

(2) To a solution of the mixture of alcohols 11 and 12 in 20 ml of methylene chloride are added 224 mg of triethylamine and 253 mg of methanesulfonyl chloride, and the mixture is stirred at room temperature for 1 hour. The mixture is washed with water, dried over Na2SO4 and concentrated under reduced pressure. The residue is chromatographed on a column of silica gel, eluting with toluene-ethyl acetate (4/1 v/v) to give 208 mg (Yield: 31%) of the objective compound (II-5) and 465 mg (Yield: 68%) of the compound 13.

$^1$HNMR (CDCl3) δ: 1.50–1.92 (m, 4H); 2.22–2.40 (m, 2H); 2.79–3.05 (m, 2H); 3.00 (s, 3H); 3.23–3.38 (m, 2H); 3.52–3.68 (m, 2H); 5.12 (s, 2H); 5.21–5.32 (m, 1H); 7.28–7.45 (m, 5H).

REFERENCE EXAMPLE 5

(1R*,5R*,6S*)-6-Phthalimido-3-trityl-3-azabicyclo[3,3,0]octane (II-6)

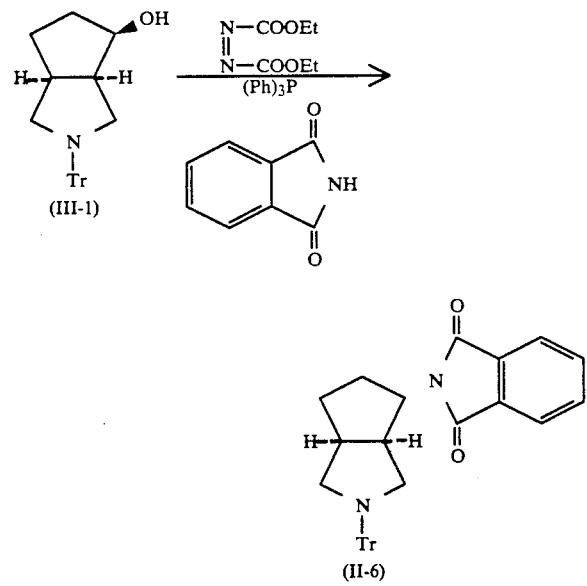

To a solution of 1 g of the compound (III-1), 710 mg of triphenylphosphine, and 3.98 g of phthalimide in 10 ml of THF is added 471 mg of diethyl azodicarboxylic acid, and the mixture is stirred at room temperature for 1.5 hours. The reaction mixture is concentrated under reduced pressure, and the residue is extracted with ether-toluene. The organic layer is concentrated, and the residue is chromatographed on a column of silica gel, eluting with n-hexane-ethyl acetate (5:1 v/v) to give 953 mg (Yield: 71%) of the objective compound (II-6).

$^1$HNMR (CDCl3) δ: 1.48–2.95 (m, 10H); 4.76–4.93 (m, 1H); 7.11–7.89 (m, 19H).

REFERENCE EXAMPLE 6

(1R*,5S*)-3-Trityl-1-carbamoyl-3-azabicyclo[3,3,0]octane (II-7)

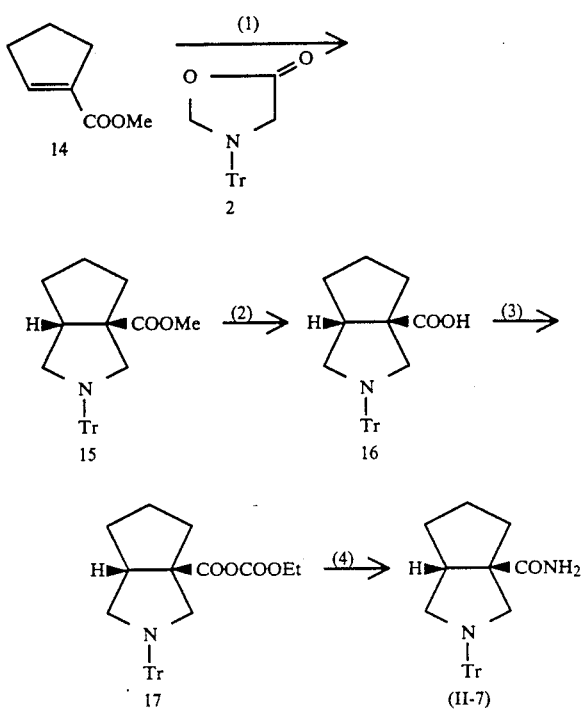

(1) A solution of 4.5 g of methyl 2-cyclopentenecarboxylate [J. Org. Chem. 35 (1970) 3352] 14 and 11.8 g of 3-(triphenylmethyl)-5-oxazolidinone 2 in 100 ml of dry toluene is refluxed for 45 hours and concentrated. The residue is chromatographed on a column of silica gel, eluting with methylene chloride-n-hexane (1:2 v/v) to give 3.9 g of the compound 15 as an oil.

IR (film): 1720, 1595 cm$^{-1}$.

$^1$HNMR (CDCl3) δ: 1.40–3.00 (m, 11H); 3.67 (s, 3H); 7.00–7.60 (m, 15H).

(2) A solution of 2.23 g of the ester 15 in 11 ml of 20% aqueous NaOH and 46 ml of methanol is refluxed for 2 hours. The solution is concentrated and neutralized with acetic acid under ice-cooling. The solution is extracted with methylene chloride, and the organic layer is washed with water, dried over Na2SO4 and concentrated. The residue is crystallized from isopropyl alcohol to give 1.8 g of the compound 16. mp. 221°–222° C. (dec.)

IR (Nujol): 3100–2500, 1685 cm$^{-1}$.

$^1$HNMR (CDCl3) δ: 1.20–3.05 (m, 11H); 7.00–7.55 (m, 15H); 1.09 (br, 1H).

(3) To a solution of 1 g of the carboxylic acid 16 in 10 ml of dry methylene chloride are added 790 mg of Et3N and 430 mg of ClCOOEt, and the mixture is refluxed for 0.5 hour. After cooling, the mixture is mixed with ice water and extracted with methylene chloride. The organic layer is washed with water, dried over Na2SO4 and concentrated to give 1.12 g of the objective compound 17 as an oil.

IR (film): 1805, 1745 cm$^{-1}$.

$^1$HNMR (CDCl3) δ: 1.35 (t, J=7.5 Hz, 3H); 1.20–2.30 (m, 8H); 2.60–3.20 (m, 3H); 4.34 (q, J=7.5 Hz, 2H); 7.05–7.60 (m, 15H).

(4) To a solution of 1.12 g of the compound 17 in 13 ml of THF is introduced ammonia gas, and the mixture is refluxed at room temperature for 10 minutes and concentrated. The residue is chromatographed on a column of silica gel, eluting with ethyl acetate-n-hexane (1:1 v/v) to give 850 mg of the compound (II-7).

IR (film): 3300, 3160, 1670 cm$^{-1}$.

$^1$HNMR (CDCl$_3$) δ: 1.00–2.40 (m, 8H); 2.60–3.20 (m, 3H); 5.92 (brs, 1H); 6.45 (brs, 1H); 7.10–7.60 (m, 15H).

REFERENCE EXAMPLE 7

(1R*,5S*)-8-Trityl-1-(N-methylcarbamoyl)-8-azabicyclo[4,3,0]nonane (II-8)

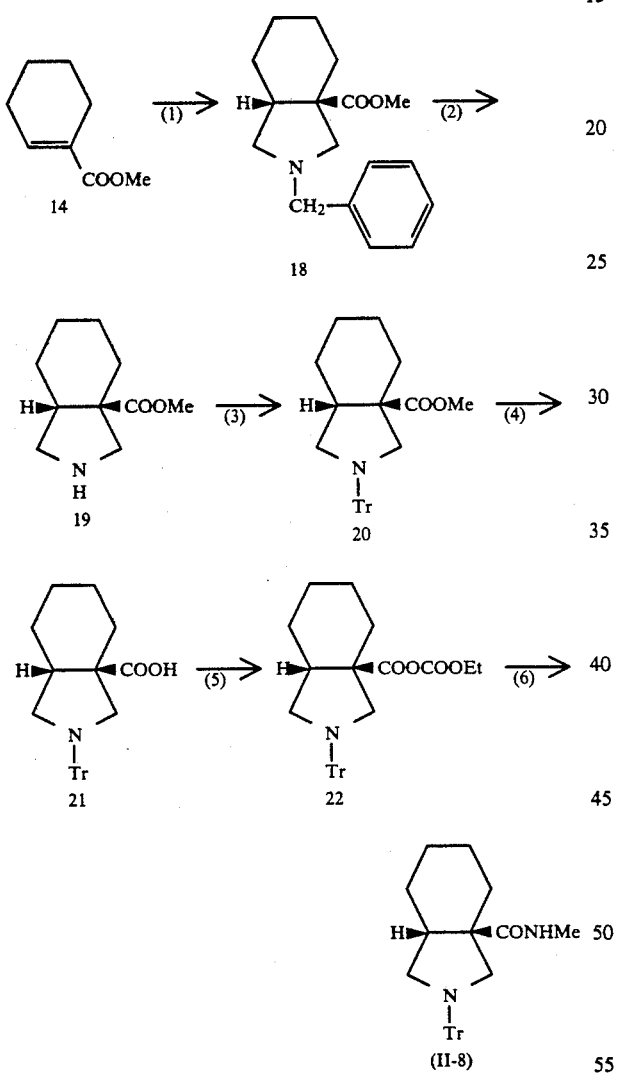

(1) To a solution of 5 g of methyl 1-cyclohexenecarboxylate 14 and 10.2 g of N-benzyl-N-(methoxymethyl)trimethylsilylamine in 100 ml of dry methylene chloride is added dropwise a mixture of 410 mg of CF$_3$COOH and 10 ml of methylene chloride, and the mixture is stirred overnight. The mixture is mixed with aqueous NaHCO$_3$ under ice-cooling and extracted with methylene chloride. The organic layer is washed with water, dried over Na$_2$SO$_4$ and concentrated. The residue is chromatographed on a column of silica gel, eluting with ethyl acetate-n-hexane (1:5 v/v) to give 1.88 g of the objective compound 18 as an oil.

IR (film): 1720, 1238 cm$^{-1}$.

$^1$HNMR (CDCl$_3$) δ: 1.20–2.00 (m, 8H); 2.60–2.95 (m, 5H); 3.60–3.73 (m, 2H); 3.68 (s, 3H); 7.20–7.32 (m, 5H).

(2) To a solution of N-benzyl compound 18 in methanol is introduced HCl gas, and excess HCl is evaporated. The residue is hydrogenated in 40 ml of methanol over 1.8 of 10% Pd-C under 5 atmospheric pressure. The reaction mixture is filtered to remove the catalyst, and the filtrate is concentrated under reduced pressure to give the objective compound 19 quantitatively as an oil.

IR (film): 3370, 1718 cm$^{-1}$.

$^1$HNMR (CD$_3$OD) δ: 1.20–2.20 (m, 8H); 2.50–3.00 (m, 1H); 3.00–5.00 (m, 4H); 3.75 (s, 3H).

(3) To a solution of 1.7 g of the compound 19 in 34 ml of dry methylene chloride are added 3.6 g of Et$_3$N and 3.3 g of trityl chloride, and the mixture is stirred at room temperature for 16 hours. And the reaction mixture is mixed with aqueous NaHCO$_3$, and extracted with methylene chloride. The organic layer is washed with water, dried over Na$_2$SO$_4$ and concentrated. The residue is chromatographed on a column of silica gel, eluting with ethyl acetate-n-hexane (1:5 v/v) to give 2.2 g of the objective compound 20 as an oil.

IR (film): 1730 cm$^{-1}$.

$^1$HNMR (CDCl$_3$) δ: 0.90–1.80 (m, 8H); 2.35–2.95 (m, 5H); 3.67 (s, 3H); 7.10–7.52 (m, 15H).

(4) A solution of 2.2 g of the compound 20 in 20 ml of 10% NaOH and 60 ml of methanol is refluxed for 3 hours, and concentrated. The residue is gradually mixed with 3 g of acetic acid, and the mixture is extracted with methylene chloride. The organic layer is washed with water, dried over Na$_2$SO$_4$, and concentrated. The residue is chromatographed on a column of silica gel, eluting with 3% methanol-methylene chloride to give the objective compound 21. It is recrystallized from n-hexane to give 1.03 g of the compound 21 as crystals. mp. 104°–106° C.

IR (NuJol): 3300–2500, 1690 cm$^{-1}$.

$^1$HNMR (CDCl$_3$) δ: 0.70–0.90 (m, 1H); 1.20–1.60 (m, 6H); 1.80–1.95 (m, 1H); 2.25–2.52 (m, 2H); 2.63–2.70 (m, 1H); 3.02–3.16 (m, 2H); 7.15–7.55 (m, 15H); 10.0 (br, 1H).

(5) To a solution of 1.1 g of the compound 21 and 810 mg of Et$_3$N in 22 ml of dry methylene chloride is added 440 mg of ClCOOEt, and the mixture is refluxed for 15 minutes and evaporated. The residue is mixed with aqueous NaHCO$_3$ and extracted with methylene chloride. The organic layer is washed with water, dried over Na$_2$SO$_4$ and concentrated to give 1.8 g of the compound 22 as an oil.

IR (film): 1795, 1742, 1070, 1010 cm$^{-1}$.

$^1$HNMR (CDCl$_3$) δ: 0.70–0.90 (m, 1H); 1.20–1.88 (m, 7H); 1.45 (t, J=7.5 Hz, 3H); 2.35–2.70 (m, 3H); 3.00–3.20 (m, 2H); 4.40 (q, J=7.5 Hz, 2H); 7.10–7.60 (m, 15H).

(6) To a solution of 1.18 g of the compound 22 in 15 ml of THF is introduced methylamine under ice-cooling, and the mixture is stirred at room temperature for 15 minutes and concentrated. The residue is extracted with methylene chloride, and the organic layer is washed with water, dried over Na$_2$SO$_4$ and concentrated. The residue is chromatographed on a column of silica gel, eluting with ethyl acetate-n-hexane (1:1 v/v) to give 500 mg of the compound (II-8) as an oil.

IR (film): 3325, 1700 cm$^{-1}$.

REFERENCE EXAMPLE 8

(1R*,5R*)-N-Trityl-1-azidocarbonyl-3-azabicyclo[3,3,-0]octane (II-9)

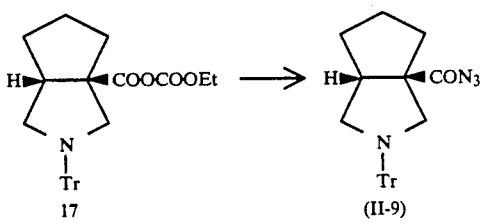

To a solution of 2.12 g of the compound 17 in 10 ml of DMF are added 1 ml of water and 910 mg of NaN₃, and the mixture is stirred at room temperature for 10 minutes. The mixture is mixed with ice water and extracted with ethyl acetate, and the organic layer is washed with water, dried over Na₂SO₄ and concentrated to give 1.71 g of the compound (II-9).

IR (film): 2120, 1700 cm⁻¹.
¹HNMR (CDCl₃) δ: 1.00–3.05 (m, 11H); 7.00–7.60 (m, 15H).

REFERENCE EXAMPLE 9

(1R*,5R*)-3-Trityl-1-ethylaminocarbonyl-3-azabicyclo[3,3,0]octane (II-10)

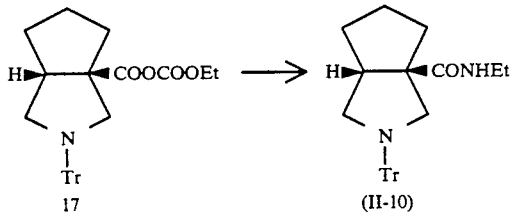

To a solution of 2.36 g of the compound 17 in 24 ml of THF is introduced ethylamine, and the mixture is stirred at room temperature for 15 minutes and concentrated. The residue is mixed with aqueous NaHCO₃ and extracted with methylene chloride. The organic layer is washed with water, dried over Na₂SO₄ and concentrated. The residue is chromatographed on a column of silica gel, eluting with 2% methanol-methylene chloride to give 2 g of the compound (II-10) as an oil.

IR (film): 3320, 1700, 1640 cm⁻¹.

REFERENCE EXAMPLE 10

(1R*,2S*,6R*)-8-Trityl-2-oxo-8-azabicyclo[4,3,0]nonane (II-11)

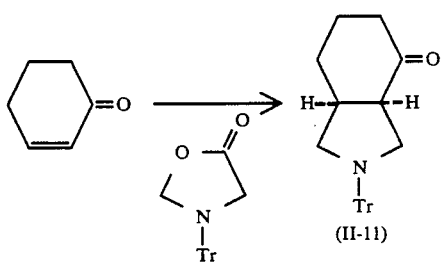

To a solution of 4.5 g of 2-cyclohexen-1-one in 155 ml of dry toluen is added 15.5 g of 3-triphenylmethyl-5-oxazolidinone, and the mixture is refluxed for 64 hours and concentrated. The residue is chromatographed on a column of silica gel, eluting with n-hexane-ethyl acetate (5:1 v/v) to give 8.5 g of the compound (II-11).

¹HNMR (CDCl₃) δ: 1.20–2.05 (m, 4H); 2.20–2.70 (m, 7H); 2.90–3.07 (m, 1H); 7.08–7.53 (m, 15H).
IR (CHCl₃): 1710, 910 cm⁻¹.

REFERENCE EXAMPLE 11

(1R*,2S*,6R*)-2-Azido-8-benzyloxycarbonyl-8-azabicyclo[4,3,0]nonane (II-12)

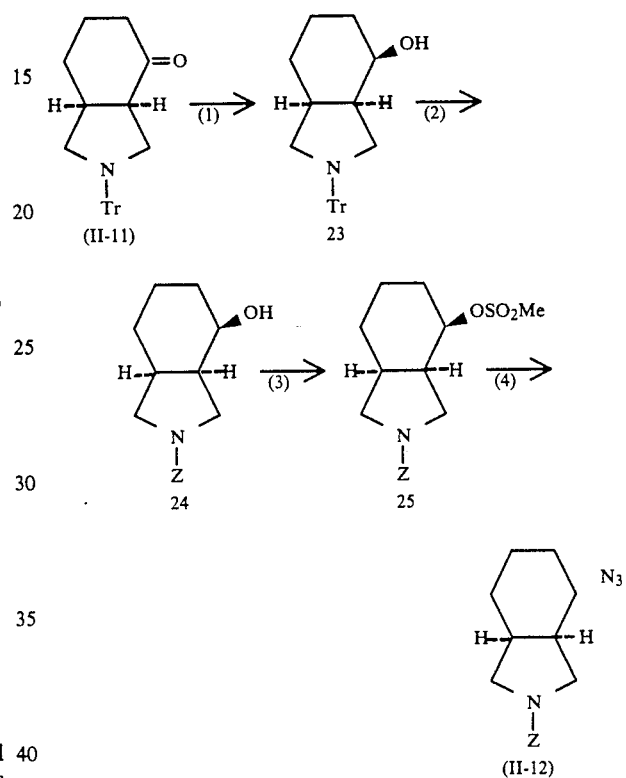

Z: —COOCH₂Ph (1) A solution of 1 g of the ketone (II-11) in 20 ml of dry THF is cooled to below −78° C. in acetone-dry ice bath and mixed dropwise with L-Selectride®. The freezing bath is released, and the mixture is stirred for 2 hours and concentrated. The residue is mixed with water and acidified with acetic acid, and the solution is stirred at room temperature for 15 minutes and basified with aqueous NaHCO₃ and extracted with methylene chloride. The organic layer is washed with water, dried over Na₂SO₄ and concentrated. The residue is chromatographed on a column of silica gel, eluting with ethyl acetate-n-hexane (1:5 v/v) to give 920 mg of the compound 23 as an oil.

¹HNMR (CDCl₃) δ: 0.80–3.0 (m, 13H); 4.00 (br, 1H); 6.90–7.60 (m, 15H).

(2) A solution of 1.7 g of the alcohol 23 in 14 ml of aqueous CF₃COOH is heated on water bath. After cooling, the solution is washed with ethyl acetate, and the aqueous layer is basified with Na₂CO₃. The solution is mixed with 830 mg of benzyl chloroformate and 10 ml of dioxane, and the mixture is stirred at room temperature for 45 minutes and extracted with methylene chloride. The organic layer is washed with water, dried over Na₂SO₄ and concentrated. The residue is chromatographed on a column of silica gel, eluting with ethyl acetate to give 1 g of the objective compound 24 as an oil.

IR (film): 3410, 1680, 1420, 1355.

¹HNMR (CDCl₃) δ: 1.10–1.80 (m, 7H); 2.09–2.22 (m, 1H); 2.50–2.70 (m, 1H); 3.30–3.60 (m, 4H); 3.90–4.00 (m, 1H); 5.08 (d, J=10 Hz, 1H); 5.19 (d, J=10 Hz, 1H); 7.30–7.40 (m, 5H).

(3) To a solution of 1 g of the alcohol 24 in 20 ml dry methylene chloride are added 1.1 g of Et₃N, and then gradually 630 mg of methanesulfonyl chloride. The mixture is stirred at room temperature for 15 minutes, mixed with aqueous NaHCO₃ and extracted with methylene chloride. The organic layer is washed with water, dried over Na₂SO₄ and concentrated. The residue is chromatographed on a column of silica gel, eluting with 3% methanol-methylene chloride to give 1.2 g of the compound 25. mp. 100°–104° C.

IR (Nujol): 1700, 1420, 1350 cm⁻¹.

¹HNMR (CDCl₃) δ: 1.05–2.00 (m, 6H); 2.20–2.30 (m, 1H); 2.75–2.90 (m, 1H); 2.99 (s, 3H); 3.30–3.65 (m, 4H); 4.90–5.08 (m, 1H); 5.14 (s, 2H); 7.03–7.40 (m, 5H).

(4) To a solution of 940 mg of the compound 25 in 9.4 ml of DMF are added 0.94 ml of water and 260 mg of NaN₃, and the mixture is stirred at 120° C. for 45 minutes and concentrated. The residue is mixed with aqueous NaHCO₃ and extracted with methylene chloride. The organic layer is washed with water, dried over Na₂SO₄ and concentrated. The residue is chromatographed on a column of silica gel, eluting with ethyl acetate-n-hexane (1:4 v/v) to give 369 mg of the objective compound (II-12) as an oil.

IR (film): 2090, 1695, 1410 cm⁻¹.

¹HNMR (CDCl₃) δ: 1.40–1.70 (m, 5H); 1.90–2.10 (m, 2H); 2.40–2.55 (m, 1H); 3.15–3.65 (m, 5H); 5.09 (d, J=10 Hz, 1H); 5.18 (d, J=10 Hz, 1H); 7.30–7.40 (m, 5H).

REFERENCE EXAMPLE 12

(1R*,2S*,7R*)-2-Oxo-N-trityl-9-azabicyclo[5,3,0]decane (II-13)

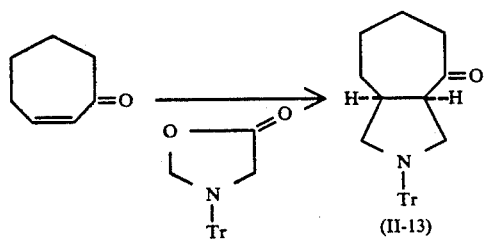

To a solution of 4.0 g of 2-cyclohepten-1-one in 120 ml of dry toluene is added 11.96 g of 3-triphenylmethyl-5-oxazolidinone, and the mixture is refluxed for 43 hours and concentrated. The residue is chromatographed on a column of silica gel, eluting with n-hexane-ethyl acetate (5:1 v/v) to give 8.4 g of the compound (II-13).

IR (CHCl₃): 1695, 900 cm⁻¹.

¹HNMR (CDCl₃) δ: 1.10–1.35 (m, 1H); 1.40–2.05 (m, 6H); 2.30–2.59 (m, 4H); 2.61–2.75 (m, 2H); 3.50–3.30 (m, 1H); 7.00–7.60 (m, 15H).

REFERENCE EXAMPLE 13

(1R*,2S*,7R*)-2-Azido-N-benzyloxycarbonyl-9-azabicyclo[5,3,0]decane (II-14)

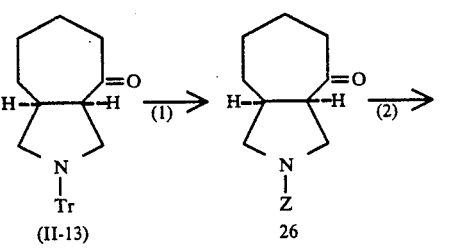

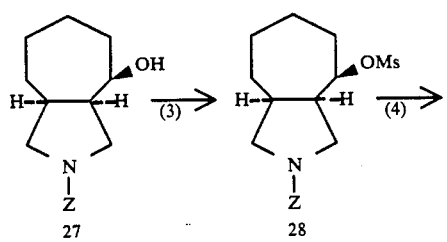

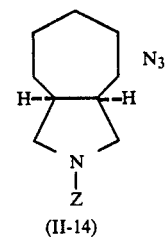

(1) To a solution of 7 g of the compound (II-13) in 40 ml of aqueous CF₃COOH is stirred at room temperature for 10 minutes and the solution is washed with ethyl acetate. The resulting aqueous layer is mixed with aqueous Na₂CO₃, 3.3 g of benzyl chloroformate, and 100 ml of dioxane, and the mixture is stirred at room temperature for 2 hours and extracted with methylene chloride. The organic layer is washed with water, dried over Na₂SO₄ and concentrated. The residue is chromatographed on a column of silica gel, eluting with ethyl acetate-n-hexane (1:1 v/v) to give 1.56 g of the compound 26.

IR (CHCl₃): 1690, 1100 cm⁻¹.

¹HNMR (CDCl₃) δ: 1.28–1.50 (m, 2H); 1.60–2.20 (m, 5H); 2.38–2.75 (m, 2H); 2.95–3.20 (m, 2H); 3.48–3.90 (m, 3H); 5.12 (s, 2H); 7.32–7.38 (m, 5H).

(2) To a solution of 1.56 g of the compound 26 in 16 ml of dry THF is added 8.1 ml of L-Selectride ® at −78° C., and the mixture is stirred at room temperature for 2 hours. The mixture is mixed with 1 ml of water, 4 ml of 30% H₂O₂, and ice water and extracted with ethyl ether. The organic layer is washed with water, dried over MgSO₄ and concentrated to give 1.65 g of the compound 27.

IR (film): 3400, 1670, 1130, 1090 cm⁻¹.

¹HNMR (CDCl₃) δ: 1.10–2.20 (m, 11H); 2.50–2.55 (m, 1H); 2.89–3.05 (m, 1H); 3.44–3.85 (m, 2H); 4.05 (bs, 1H); 5.12 (s, 2H); 7.32–7.38 (m, 5H).

(3) To a solution of 1.65 g of the compound 27 in 33 ml of dry methylene chloride are added 864 mg of Et₃N, and subsequently 780 mg of CH₃SO₂Cl under ice-cooling, and the mixture is stirred at room temperature for 30 minutes. The mixture is mixed with aqueous $NaHCO_3$ and extracted with methylene chloride. The organic layer is washed with water, dried over $Na_2SO_4$ and concentrated. The residue is chromatographed on a column of silica gel, eluting with ethyl acetate-n-hexane (1:1 v/v) to give 1.7 g of the compound 28.

IR (film): 1690, 1160, 1095, 880 $cm^{-1}$.

$^1$HNMR ($CDCl_3$) δ: 1.20–1.40 (m, 1H); 1.45–2.00 (m, 7H); 2.06–2.50 (m, 3H); 2.95–3.05 (m, 1H); 3.02 (s, 3H); 3.62–3.85 (m, 2H); 5.03–5.07 (m, 1H); 5.11 (s, 2H); 7.32–7.38 (m, 5H).

(4) To a solution of 1.7 g of the compound 28 in 20 ml of DMF is added 903 mg of NaH in 20 ml of water, and the mixture is heated at 120° C. for 2 hours, mixed with ice water and extracted with ethyl ether. The organic layer is washed with water, dried over $MgSO_4$ and concentrated. The residue is chromatographed on a column of silica gel, eluting with ethyl acetate-n-hexane (1:4 v/v) to give 1.2 g of the compound (II-14).

IR (Nujol): 2075, 1690, 1125, 1095 $cm^{-1}$.

$^1$HNMR ($CDCl_3$) δ: 1.20–2.13 (m, 10H); 2.90–3.30 (m, 3H); 3.65–3.98 (m, 2H); 5.12 (s, 2H); 7.32–7.38 (m, 5H).

REFERENCE EXAMPLE 14

N-Benzoyl-4-azidooctahydroindole (II-15)

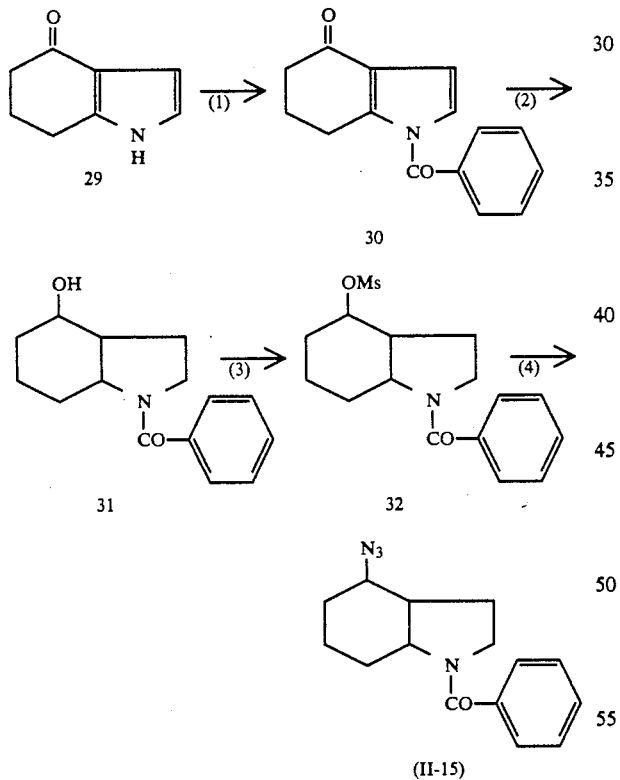

(1) To a solution of 5 g of 4-oxo-4,5,6,7-tetrahydroindole 29 (J. Org. Chem. Vol. 43, No. 18 (1978) 3541) in 25 ml of dry dimethylformamide is added 1.8 g of 60% NaH, and the mixture is stirred for 5 minutes. The mixture is added dropwise with 6.2 g of benzoyl chloride and stirred at room temperature for 10 minutes. The mixture is poured into ice water, and the solution is extracted with ether. The organic layer is washed with water, dried over $Na_2SO_4$ and concentrated. The residue is crystallized from ethyl acetate-isopropyl alcohol to give 6.5 g (Yield: 73%) of the compound 30. mp. 121°–122° C.

$^1$HNMR ($CDCl_3$) δ: 1.90–2.60 (m, 4H); 3.15–3.27 (m, 2H); 6.58 (d, J=4.5 Hz, 1H); 6.87 (d, J=4.5 Hz, 1H); 7.40–7.80 (m, 5H).

IR (Nujol): 1690, 1650 $cm^{-1}$.

(2) A solution of 5 g of the compound 30 in 50 ml of acetic acid is hydrogenated over 1 g of $PtO_2.H_2O$ under 5 atmospheric pressure. The mixture is filtered to remove the catalyst, and the filtrate is concentrated. The residue is mixed with aqueous $NaHCO_3$ and extracted with methylene chloride. The organic layer is washed with water, dried over $Na_2SO_4$ and concentrated. The residue is chromatographed on a column of silica gel, eluting with ethyl acetate ~ 5% methanol-ethyl acetate and concentrated to give 6.3 g of the objective compound 31 as an oil.

IR (film): 3370, 1650, 1435, 790 $cm^{-1}$.

$^1$HNMR ($CDCl_3$) δ: 0.90–2.70 (m, 9H); 3.20–4.50 (m, 5H); 7.30–7.50 (m, 5H).

(3) To a solution of 5.5 g of the compound 31 in 40 ml of dry methylene chloride are added 3.3 g of $Et_3N$, and subsequently 3.76 g of $MeSO_2Cl$ under ice-cooling, and the mixture is stirred for 15 minutes. The mixture is mixed with aqueous $NaHCO_3$ and extracted with methylene chloride. The organic layer is washed with water, dried over $Na_2SO_4$ and concentrated. The residue is chromatographed on a column of silica gel, eluting with methylene chloride ~ 3% methanol-methylene chloride to give 5.9 g of the objective compound 32 as an oil.

IR (film): 1620, 1420, 1345, 1170, 790 $cm^{-1}$.

$^1$HNMR ($CDCl_3$) δ: 0.90–2.40 (m, 9H); 2.60–2.90 (m, 1H); 3.04 (s, 3H); 3.30–3.80 (m, 2H); 4.80–5.05 (m, 1H); 7.35–7.50 (m, 5H).

(4) To a solution of 5.9 g of the compound 32 in 59 ml of DMF is added a solution of 1.75 g of $NaN_3$ in 5.9 ml of water, and the mixture is heated at 120° C. for 20 minutes and concentrated. The residue is chromatographed on a column of silica gel, eluting with ethyl acetate-n-hexane (1:2 v/v) ~ ethyl acetate-n-hexane (1:1 v/v) to give 1.3 g of the objective compound (II-15) as an oil.

IR (film): 2075, 1620, 1410, 780 $cm^{-1}$.

$^1$HNMR ($CDCl_3$) δ: 1.20–2.40 (m, 9H); 3.30–4.00 (m, 4H); 7.30–7.50 (m, 5H).

What is claimed is:

1. A compound of the formula

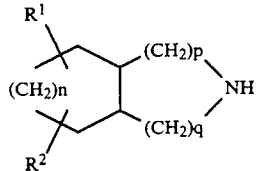

wherein $R^1$ is hydrogen or hydroxy; $R^2$ is amino or aminomethyl, each of which is substituted by one or two members selected from the group consisting of methyl, ethyl, propyl, formyl and acetyl; n is an integer of 1 to 3; p and q each is an integer of 0 to 2 with the proviso that p+q=2 or an acid-addition salt thereof.

2. A compound claimed in claim 1, in which said compound is represented by the formula:

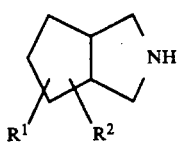

wherein $R^1$ is the same as defined in claim 1 and $R^2$ is amino or aminomethyl, each of which is substituted by one or two members selected from the group consisting of methyl, ethyl, formyl and acetyl.

3. A compound claimed in claim 2, which is 6-acetylamino-3-azabicyclo[3,3,0]octane.

4. A compound claimed in claim 2, which is 6-(N-methylacetylamino)-3-azabicyclo[3,3,0]octane.

5. A compound claimed in claim 2, which is 1-acetylaminomethyl-3-azabicyclo[3,3,0]octane.

6. A compound claimed in claim 2, which is 1-(N-formyl-N-methylaminomethyl)-3-azabicyclo[3,3,0]octane.

7. A compound claimed in claim 2, which is 1-(N-formyl-N-ethylaminomethyl)-3-azabicyclo[3,3,0]octane.

8. A compound claimed in claim 1, in which said compound is represented by the formula:

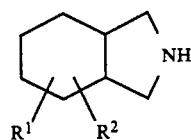

wherein $R^1$ is the same as defined in claim 1 and $R^2$ is amino substituted by one or two members selected from the group consisting of methyl, ethyl, formyl and acetyl.

9. A compound claimed in claim 8, which is 2-formylamino-8-azabicyclo[4,3,0]nonane.

10. A compound claimed in claim 8, which is 2-(N-methylformylamino)-8-azabicyclo[4,3,0]nonane.

11. A compound claimed in claim 1, in which said compound is represented by the formula:

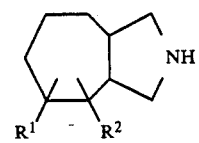

wherein $R^1$ is the same as defined in claim 1 and; $R^2$ is amino substituted by one or two members selected from the group consisting of methyl, ethyl, formyl and acetyl.

12. A compound claimed in claim 11, which is 2-formylamino-9-azabicyclo[5,3,0]decane.

* * * * *